(12) United States Patent
Sugiki et al.

(10) Patent No.: US 6,710,056 B2
(45) Date of Patent: Mar. 23, 2004

(54) AMIDINOPHENYLPYRUVIC ACID DERIVATIVES

(75) Inventors: Masayuki Sugiki, Kawasaki (JP); Kazuyuki Sagi, Kawasaki (JP); Kohichi Fujita, Kawasaki (JP); Takashi Kayahara, Kawasaki (JP); Shunji Takehana, Kawasaki (JP); Kuniya Sakurai, Kawasaki (JP); Kazumi Tashiro, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/161,779

(22) Filed: Jun. 5, 2002

(65) Prior Publication Data

US 2003/0109547 A1 Jun. 12, 2003

Related U.S. Application Data

(63) Continuation of application No. PCT/JP00/08569, filed on Dec. 4, 2000.

(30) Foreign Application Priority Data

Dec. 6, 1999 (JP) ............................................ 11-346152

(51) Int. Cl.⁷ ........................ C07D 215/48; A61K 31/47
(52) U.S. Cl. ........................ 514/311; 307/317; 307/365; 307/399; 307/568; 307/621; 546/146; 546/168; 546/187; 548/309.4; 548/200; 562/440; 564/169
(58) Field of Search ............................ 546/146, 187, 546/168; 514/307, 317, 311, 365, 399, 568, 621; 548/309.4, 200; 562/440; 564/169

(56) References Cited

FOREIGN PATENT DOCUMENTS

| WO | 98/31661 | 7/1998 |
|---|---|---|
| WO | 99/64392 | 12/1999 |

*Primary Examiner*—Zinna Northington Davis
(74) *Attorney, Agent, or Firm*—Oblon, Spivak, McClelland, Maier & Neustadt, P.C.

(57) ABSTRACT

An amidinophenylpyruvic acid derivative of the following formula, analogs thereof and pharmaceutically acceptable salts thereof have an excellent antagonistic effect against activated blood coagulation factor VII.

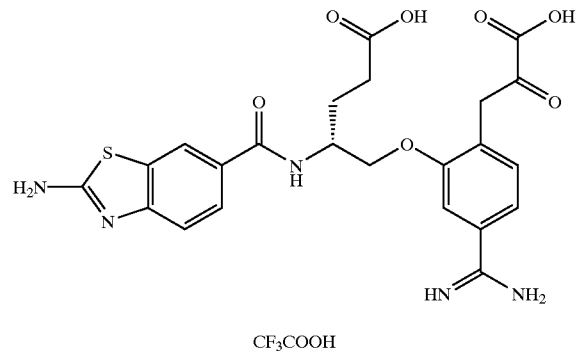

34 Claims, No Drawings

AMIDINOPHENYLPYRUVIC ACID DERIVATIVES

BACKGROUND OF THE INVENTION

The present invention relates to new amidinophenylpyruvic acid derivatives antagonistic to activated blood coagulation factor VII (FVIIa) and pharmaceutically acceptable salts thereof. The amidinophenylpyruvic acid derivatives and salts thereof of the present invention are usable as active ingredients of blood anticoagulants, pharmaceutical composition for preventing or treating a thrombus or embolus, intimal thickening inhibitors or pharmaceutical composition for preventing or treating angiostenosis and vascular occlusion.

When a thrombus or embolus is formed in a blood vessel, the normal blood flow becomes impossible to cause various diseases. The anticoagulation therapy is one of internal medical treatment methods for treating and preventing thrombosis like fibrinolytic therapy and antiplatelet therapy.

Anticoagulants available on the market are warfarin capable of inhibiting the formation of coagulation factors, thrombin inhibitors, etc. However, they often have undesirable side effects such as causing of serious hemorrhage and, therefore, they cannot easily control of the coagulating property. Now, it is demanded in the art to find a compound having an anticoagulating activity based on a new function mechanism and free of the undesirable side effects of the existing anticoagulants. It is also demanded in the art to find an anticoagulating compound having a high peroral activity and free of undesirable side effects.

The blood coagulation paths are roughly divided into intrinsic path and extrinsic path. Although the relative importance of each of the two coagulation paths has not yet been elucidated, it is said that the extrinsic coagulating reaction is deeply concerned in the acceleration of coagulation. The origin of the extrinsic coagulating reaction is the incidence of glycoprotein tissue factor (TF) on the surface of a cell membrane. When FVIIa and TF form a complex (FVIIa/TF) together, the activation is further accelerated. The complex having serine protease-type activity specifically reacts on blood coagulation factors X and IX to activate the respective factors. As a result, thrombin is activated to form a thrombus. The term "inhibition of activated blood coagulation factor VII (FVIIa inhibition)" herein indicates the inhibition of the activity of FVIIa/TF complex enzyme.

Thus, compounds having the FVIIa inhibition activity have an excellent blood anticoagulating activity, and they will be possibly used as medicines free of the defects of ordinary anticoagulants. Further, medicines capable of selectively inhibiting FVIIa will be possibly used as excellent anticoagulating medicines substantially free from side effects.

Disseminated intravascular coagulation is usually caused because a tissue factor forms a complex with FVIIa in the blood, and an FVIIa inhibitor is possibly particularly effective against generalized intravascular blood coagulation syndrome.

It is known that thrombi are hardly formed in the blood of patients lacking in VII factor at a high shear rate. The FVIIa inhibitor is possibly effective in controlling the thrombus formation particularly in narrowed arteries (R. Bastad et al., Blood. 84, 3371 (1994)).

The FVIIa inhibitor is possibly effective in controlling the restenosis after angioplasty with, for example, a balloon catheter (Y. Jang et al., Circulation 92, 3041 (1995) and D. W. Courtman et al., Circ Res. 82, 996 (1998)).

It is known that FVIIa/TF causes the migration of smooth muscle cells of blood vessels. The activity of a compound to inhibit this effect can be examined by a method described in Sato Y et al., Thromb Haemost. 78, 1138 (1997). FVIIa inhibitor might be effective in not only inhibiting the thrombus formation but also controlling the thickening of intima by inhibiting the migration of smooth muscles to control the narrowing or occlusion of the blood vessels.

However, compounds clinically usable as FVIIa inhibitor have not been obtained yet.

DISCLOSURE OF THE INVENTION

An object of the present invention is to provide compounds having an excellent effect of inhibiting the action of activated blood coagulation factor VII.

Another object of the present invention is to provide compounds capable of selectively inhibiting activated blood coagulation factor VII.

A third object of the present invention is to provide peroral compounds selectively inhibiting the action of activated blood coagulation factor VII.

A fourth object of the present invention is to provide a pharmaceutical composition.

A fifth object of the present invention is to provide a pharmaceutical composition for preventing or treating diseases caused by the blood coagulation, thrombus or embolus, intimal thickening or angiostenosis.

A sixth object of the present invention is to provide a pharmaceutical composition for preventing or treating disseminated intravascular coagulation, deep vein thrombosis, diseases caused by pulmonary vascular disorder, diseases caused by an ischemic heart disease, diseases caused by a cerebrovascular disorder, occlusion of blood vessel and angiostenosis after an operation for forming a bypass in coronary artery, coronary artery intervention after percutaneous transluminal coronary angioplasty (PTCA), occlusion of blood vessel and angiostenosis after percutaneous transluminal coronary recanalization (PTCR), formation of thrombi after artificial blood vessel-forming operation or artificial valve replacement, peripheral embolism, formation of thrombi in the course of the extracorporeal circulation and antiphospholipid antibody syndrome.

A seventh object of the present invention is to provide a pharmaceutical composition for preventing or treating cerebral infarction or cerebral stroke.

A eighth object of the present invention is to provide an antagonist against activated blood coagulation factor VII (FVIIa).

Under these circumstances, the inventors made investigations on FVIIa inhibiting activity of benzamidine derivatives disclosed in WO 98/31661 as compounds having an effect of inhibiting activated blood coagulation factor X (FXa). As a result, the inventors found that only specified amidinophenylpyruvic acid derivatives have a high activity of inhibiting FVIIa. After synthesizing the new amidinophenylpyruvic acid derivatives and examining the effect thereof on extrinsic blood coagulation factors on the basis of these facts, the inventors have found that they are highly useful new compounds having an activation profile different from that of ordinary ones. Namely, these compounds have a high activity of inhibiting FVIIa and a high selectivity toward thrombin. The present invention has been completed on the basis of these findings.

The present invention provides amidinophenylpyruvic acid derivatives of the following general formula (1) or (1-2), pharmaceutically acceptable salts thereof and an antagonist against activated blood coagulation factor VII (FVIIa), which contains such a compound(s) as the active ingredient:

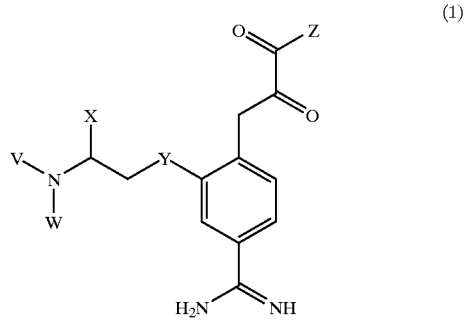

(1)

wherein W represents a hydrogen atom or an alkyl group having 1 to 6 carbon atoms, X represents a hydrogen atom, a carboxyalkyl group having 2 to 5 carbon atoms, or a methyl or ethyl group having a substituent(s) selected from the group consisting of alkoxycarbonyl groups having 2 to 8 carbon atoms, carbamoyl group, tetrazolyl group, sulfo group, sulfamoyl group, phosphono group and hydroxyl group, a benzyl group which may have a substituent(s) selected from the group consisting of hydroxyl group, carboxyl group, tetrazolyl group, sulfo group, sulfamoyl group, phosphono group, halogeno groups and alkyl groups having 1 to 3 carbon atoms, or an alkyl group having 1 to 4 carbon atoms, phenyl group, guanidinopropyl group, mercaptomethyl group, imidazolylmethyl group, aminobutyl group, aminopropyl group, (methylthio)ethyl group or indolylmethyl group, X and W may be bonded together to form a ring, and in this case, —W—X— represents ethylene group, trimethylene group or tetramethylene group, V represents any of the following groups (1) to (8):

(1) benzimidazolecarbonyl, quinolinecarbonyl, benzothiazolecarbonyl or benzoxazolecarbonyl group which may have a substituent(s) selected from the group consisting of amino group, alkyl groups having 1 to 6 carbon atoms, halogeno groups and alkoxyl groups having 1 to 6 carbon atoms, (2) benzoyl group substituted with phenyl, pyridyl or thiophenyl group having a substituent(s) selected from the group consisting of amidino group, guanidino group, amino group, dialkylamino groups having 2 to 5 carbon atoms, carboxyl group and acyl groups having 1 to 6 carbon atoms, (3) benzoyl group substituted with phenoxymethyl or benzoylamino group which may have a substituent(s) selected from the group consisting of amidino group, methoxyl group, guanidino group, amino group and dialkylamino groups having 2 to 5 carbon atoms, (4) guanidinocarbonylbenzoyl group or (guanidinomethyl) benzoyl group, (5) a monoalkylguanidinobenzoyl group having 9 to 11 carbon atoms wherein the alkyl group bonded to the guanidino group may be also bonded to benzoyl group to form a ring, (6) naphthalenecarbonyl, thiophenecarbonyl or 1-naphthalenesulfonyl group which may have a substituent(s) selected from the group consisting of guanidino group, guanidinocarbonyl group, guanidinomethyl group and amidino group, (7) benzoyl group which may have a substituent(s) selected from the group consisting of hydroxyl group, N-methylpyrrolidyloxy group, pyrrolidylmethyl group, imidazolylmethyl group and aminoimidazolylmethyl group, and (8) dihydrobenzofurancarbonyl or dihydrobenzopyrancarbonyl group which may have a substituent(s) selected from the group consisting of amidino group, guanidino group, amino group, alkyl groups having 1 to 6 carbon atoms, halogeno groups and aryl groups having 4 to 6 carbon atoms, groups (1) to (7) described above may further have an alkoxyl group having 1 to 6 carbon atoms on an aromatic carbon at the o-position to the carbonyl group or sulfonyl group bonded to N in general formula (1), and when the alkyl group on the alkoxyl group has 2 or 3 carbon atoms, it may be bonded to a carbon atom on the aromatic ring to form a ring, Y represents oxygen atom or sulfur atom, and Z represents hydroxyl group or amino group which may have a substituent(s) selected from the group consisting of phenyl group, benzyl group and phenethyl group, or

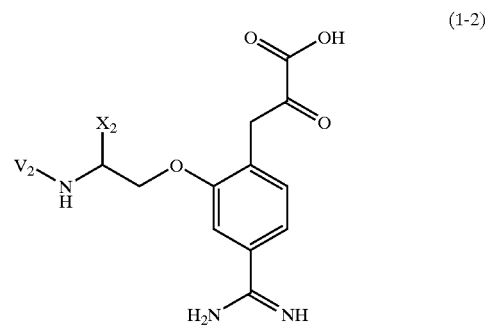

(1-2)

wherein $X_2$ represents hydrogen atom, carboxymethyl group or carboxyethyl group, and $V_2$ represents benzoyl group having a substituent(s) selected from the group consisting of alkoxyl groups having 1 to 5 carbon atoms at the o-position to the carbonyl group in benzoyl group, iodine atom or phenyl, thiophenyl, pyridyl or guanidino group at the m-position to the carbonyl group in benzoyl group, or guanidino or amino group at the p-position to the carbonyl group in benzoyl group, or $V_2$ represents 1-(4-pyridyl)piperidine-3-carbonyl group or indole-5-carbonyl group.

BEST MODE FOR CARRYING OUT THE INVENTION

In general formula (1), W is preferably hydrogen atom or an alkyl group having 1 to 3 carbon atoms. Hydrogen is particularly preferred.

In general formula (1), Y is preferably oxygen atom.

In general formula (1), preferably, W is hydrogen atom and Y is oxygen atom.

In general formula (1), the carboxyalkyl group X having 2 to 5 carbon atoms is preferably that having 2 to 4 carbon atoms. The carboxyalkyl group X is more preferably carboxymethyl group or carboxyethyl group. X is preferably hydrogen atom, carboxymethyl group or carboxyethyl group. X is more preferably carboxyethyl group, and in particular, (R)-carboxyethyl group.

In general formula (1), V is preferably benzoyl group having a substituent(s) derived from guanidino group, benzoyl group having an aryl group having a substituent(s) or phenoxymethyl group having a substituent(s) at the 3-position or a group composed of benzoyl group condensed with a five-membered or six-membered aromatic heterocyclic ring.

An example wherein an alkoxyl group having 1 to 6 carbon atoms in the groups of above formulae (1) to (7) is bonded to an aromatic carbon at the o-position to carbonyl group bonded to N in general formula (1) is 2-Methoxy-3-(4-amidinophenyl)benzoyl group when V is 3-(4-amidinophenyl)benzoyl group.

V in general formula (1) is preferably as follows:

Benzimidazolecarbonyl, quinolinecarbonyl or benzothiazolecarbonyl group which may have a substituent(s); the substituent being selected from the group consisting of amino group, alkyl groups having 1 to 6 carbon atoms, halogeno groups and alkoxyl groups having 1 to 6 carbon atoms;

Benzoyl group substituted with phenyl, pyridyl or thiophenyl group, having a substituent(s), at the 3-position thereof; the substituent being amidino group, guanidino group or amino group;

Benzoyl group substituted with phenoxymethyl group, having a substituent(s), at the 3-position thereof; the substituent being amidino group, guanidino group or amino group;

Guanidinocarbonylbenzoyl group or (guanidinomethyl) benzoyl group;

Naphthalenecarbonyl or thiophenecarbonyl group having a substituent(s): the substituent being guanidino group, guanidinocarbonyl group or guanidinomethyl group; or A monoalkylguanidinobenzoyl group having 9 to 11 carbon atoms, wherein the alkyl group bonded to guanidino group may be also bonded to benzoyl group to form a ring.

V in general formula (1) is preferably as follows:

Benzimidazole-5-carbonyl, quinoline-6-carbonyl or benzothiazole-6-carbonyl group which may have a substituent(s); the substituent being an amino group(s), an alkyl group(s) having 1 to 6 carbon atoms, a halogeno group(s) or an alkoxyl group(s) having 1 to 6 carbon atoms;

Benzoyl group substituted with phenyl, pyridyl or thiophenyl group, having a substituent(s), at the 3-position thereof; the substituent being amidino group or guanidino group;

Benzoyl group substituted with phenoxymethyl group, which may have a substituent(s), at the 3-position thereof; the substituent being amidino group or guanidino group;

3-Guanidinocarbonylbenzoyl group or 3-guanidinomethylbenzoyl group; or

1-Amidino-1,2,3,4-tetrahydroquinoline-6-carbonyl group.

V in general formula (1) is more preferably as follows:

Benzimidazole-5-carbonyl, quinoline-6-carbonyl or benzothiazole-6-carbonyl group which may have a substituent(s); the substituent being an amino group(s) or an alkyl group(s) having 1 to 3 carbon atoms, Benzoyl group substituted with phenyl or pyridyl group, having a substituent which is amidino group or guanidino group, at the 3-position;

3-Guanidinocarbonylbenzoyl group or

1-Amidino-1,2,3,4-tetrahydroisoquinoline-6-carbonyl group.

In general formula (1), V is particularly preferably benzothiazole-6-carbonyl group.

In general formula (1), Z is preferably hydroxyl group.

Preferred amidinophenylpyruvic acid derivatives of the above formula (1) and pharmaceutically acceptable salts thereof are those of general formula (1) wherein:

W represents hydrogen atom or an alkyl group having 1 to 3 carbon atoms,

X represents hydrogen atom or a carboxyalkyl group having 2 to 5 carbon atoms,

V represents benzimidazolecarbonyl, quinolinecarbonyl or benzothiazolecarbonyl group which may have a substituent(s); the substituent being an amino group(s), an alkyl group(s) having 1 to 6 carbon atoms, a halogeno group(s) or an alkoxyl group(s) having 1 to 6 carbon atoms, benzoyl group substituted with phenyl, pyridyl or thiophenyl group having a substituent, at the 3-position thereof, the substituent being amidino group, guanidino group or amino group, benzoyl group substituted with phenoxymethyl group having a substituent(s), at the 3-position thereof, the substituent being amidino group, guanidino group or amino group, guanidinocarbonylbenzoyl group or (guanidinomethyl) benzoyl group, naphthalenecarbonyl or thiophenecarbonyl group having a substituent(s);

the substituent being guanidino group, guanidinocarbonyl group or guanidinomethyl group, or a monoalkylguanidinobenzoyl group having 9 to 11 carbon atoms, wherein the alkyl group bonded to guanidino group may be also bonded to benzoyl group to form a ring, and Z represents hydroxyl group.

More preferred compounds are as follows:

compounds of general formula (1) wherein X is limited to a group listed above to be preferred as X, compounds of general formula (1) wherein Y and W are each limited to a group listed above to be preferred, and compounds of general formula (1) wherein V is limited to a group listed above to be preferred.

Further, the following compounds of general formula (1) are preferred:

W represents hydrogen atom,

X represents hydrogen atom or carboxyethyl group,

V represents benzimidazole-5-carbonyl, quinoline-6-carbonyl or benzothiazole-6-carbonyl group which may have a substituent(s); the substituent being amino group or an alkyl group having 1 to 3 carbon atoms, Y represents oxygen atom, and Z represents hydroxyl group.

Preferred amidinophenylpyruvic acid derivatives of the above formula (1) and pharmaceutically acceptable salts thereof are those wherein:

W represents hydrogen atom,

X represents hydrogen atom or carboxyethyl group,

V represents 3-guanidinocarbonylbenzoyl group, 3-guanidinomethylbenzoyl group, 3-(4-amidinophenoxymethyl)benzoyl group, benzimidazole-5-carbonyl group, 2-methylbenzimidazole-5-carbonyl group, 2-aminobenzimidazolecarbonyl group, 2-aminoquinoine-6-carbonyl group, 3-(4-amidinophenyl)benzoyl group, 3-(4-guanidinophenyl)benzoyl group, 1-amidino-1,2,3,4-tetrahydroquinoline-6-carbonyl group or 2-aminobenzothiazole-6-carbonyl group, Y represents oxygen atom, and Z represents hydroxyl group.

Preferred amidinophenylpyruvic acid derivatives of the above formula (1) and pharmaceutically acceptable salts thereof are those wherein:

W represents hydrogen atom,

X represents carboxyethyl group,

V represents 2-methylbenzimidazole-5-carbonyl group, 2-amiobenzimidazole-5-carbonyl group, 2-aminoquinoline-6-carbonyl group or 2-aminobenzothiazole-6-carbonyl group, Y represents oxygen atom and Z represents hydroxyl group.

In general formula (1-2), $X_2$ is preferably carboxyethyl group or hydrogen atom, and when $V_2$ represents benzoyl group having a substituent(s), the substituent is preferably 3-phenyl group, 2-isopropoxy group, 2-cyclopentyloxy group or 4-guanidino group.

Compounds of general formula (1) or (1-2) are preferably those described in Examples, though the compounds are not limited to them. Compounds described in Examples 1, 2, 3, 4, 13, 27, 28 and 39 are preferred. The compound described in Example 28 is particularly preferred.

The alkyl groups and alkoxyl groups in the compounds of the present invention may be branched or they may have a ring. For example, alkyl groups include, for example, isopropyl group, and alkoxyl groups include, for example, cyclobutyloxy group. In dialkylamino groups, two alkyl groups may be bonded to each other to form a ring such as 1-pyrrolidyl group. The halogeno groups include fluorine atom, chlorine atom and bromine atom. In the monoalkylguanidinobenzoyl groups, the alkyl group may be bonded to guanidino group and benzoyl group to form a ring. In this case, an aromatic hydrocarbon at the o-position to guanidino group is bonded to one of the nitrogen atoms in guanidino group through methylene, ethylene or triethylene group. Examples of these groups are 1-amidino-1,2,3,4-tetrahydroquinolinecarbonyl group and 2-amino-3,4-dihydroquinazolinecarbonyl group.

The compounds of the present invention include mixtures of various stereoisomers such as geometrical isomers, tautomers and optical isomers, as well as isolated ones. Amidino group in the compounds of the present invention may be replaced with a suitable substituent capable of being changed into the amidino group in vivo. For example, in general formulae (1) and (1-2), hydrogen atom bonded to nitrogen atom having double bond in amidino group bonded to benzene ring may be replaced with hydroxyl group, an alkoxyl group such as ethoxyl group, amino group, carboxyl group, an alkoxycarbonyl group such as ethoxycarbonyl group, an alkylsulfonyl group such as ethylsulfonyl group, carbamoyl group, a carbamoyl group in which one or two hydrogen atoms are replaced with an alkyl group such as diethoxycarbamoyl group, formyl group, an acyl group such as acetyl group and an alkylcarboxyl group such as acetoxyl group.

The salts of amidinophenylpyruvic acid derivatives represented by general formula (1) or (1-2) are pharmaceutically acceptable salts such as salts thereof with mineral acids, e.g. hydrochloric acid, hydrobromic acid, sulfuric acid, nitric acid and phosphoric acid; salts thereof with organic acids, e.g. formic acid, acetic acid, lactic acid, salicylic acid, mandelic acid, citric acid, oxalic acid, maleic acid, fumaric acid, tartaric acid, tannic acid, malic acid, tosyl acid, methanesulfonic acid and benzenesulfonic acid; salts thereof with alkali metals, alkaline earth metals and alkylammonium groups, e.g. sodium, potassium, calcium, ammonium and triethylammonium group; and hydrates thereof.

Typical processes for producing the compounds of the present invention will be described below.

An amino acid (2) in which nitrogen atom is protected with t-butoxycarbonyl group or the like can be synthesized from a well-known amino acid derivative by an ordinary method. The amino acid (2) is subjected to a proper reduction reaction such as a reaction with ethyl chloroformate in the presence of, for example, a base to activate carboxyl group and to form a mixed acid anhydride, followed by the treatment with NaBH4. Thus an alcohol compound (3) can be obtained. The alcohol compound (3) is reacted with, for example, carbon tetrabromide in the presence of triphenylphosphine or with methanesulfonyl chloride in the presence of a base to obtain a compound (4) having a leaving group such as bromine atom, methanesulfonyloxy group or chlorine atom in place of hydroxyl group.

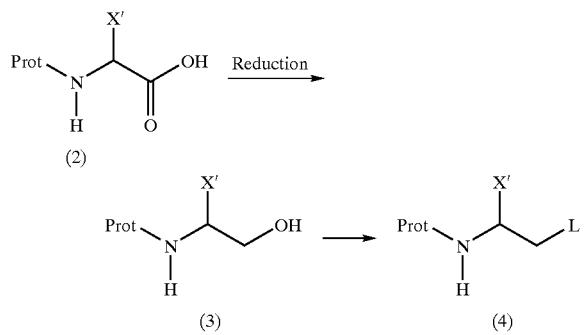

wherein Prot represents a protecting group, X' is the same as X or it represents a group obtained by protecting a functional group in X, and L represents a leaving group.

The compound (4) thus obtained is reacted with 3-hydroxy-4-iodobenzonitrile in the presence of a base such as potassium carbonate in a solvent such as dimethylformamide to form an ether compound (5).

The ether compound (5) thus obtained can be converted into an acrylic acid ester derivative (6) by condensing it by, for example, Mizorogi-Heck reaction with methyl 2-acetamidoacrylate in the presence of palladium catalyst.

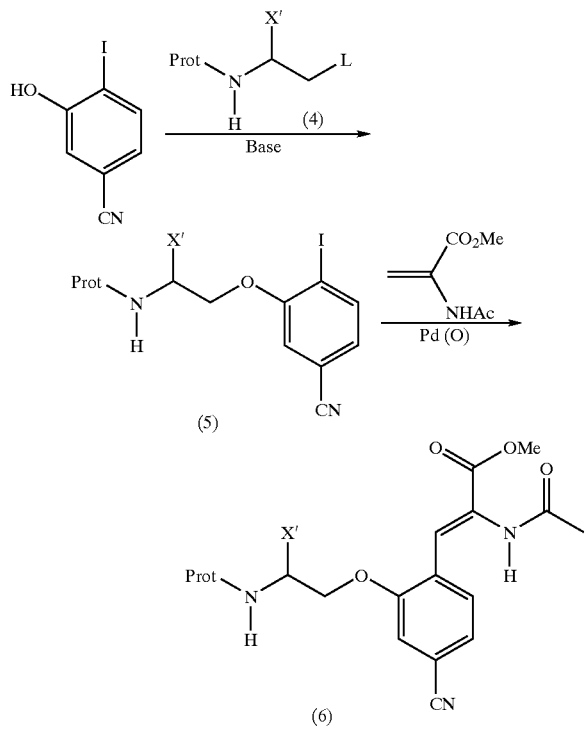

(4)

(5)

(6)

An amine (7) can be obtained by removing the protecting group on nitrogen in the acrylic acid ester derivative (6) with, for example, an acid solvent such as hydrogen chloride-containing dioxane solvent.

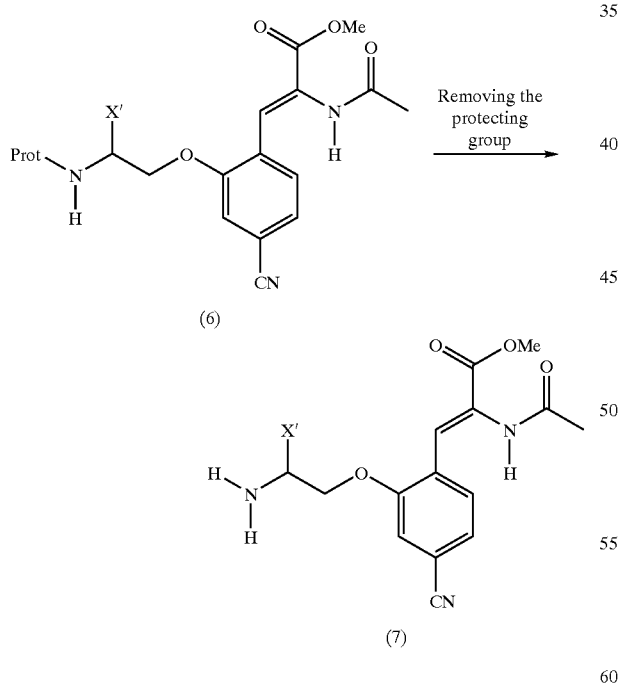

(6)

(7)

In the production of a compound of general formula (1) wherein W represents an alkyl group having 1 to 6 carbon atoms, the amine (7) obtained as described above is subjected to the reductive amination with paraformaldehyde or an alkylaldehyde and sodium cyanoborohydride or the like to obtain the compound of general formula (8) wherein W represents an alkyl group having 1 to 6 carbon atoms:

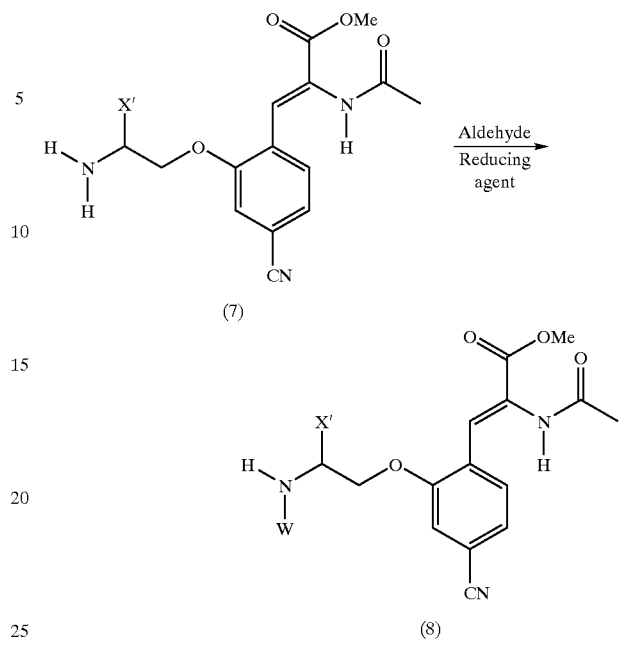

(7)

(8)

wherein W represents an alkyl group having 1 to 6 carbon atoms.

Thus obtained amine (8) wherein W represents a hydrogen atom or an alkyl group having 1 to 6 carbon atoms is condensed with a suitable carboxylic acid in the presence of a condensing agent such as dicyclohexylcarbodiimide in a solvent such as methylene chloride or dimethylformamide, or it is reacted with a suitable sulfonyl chloride or an acid halide in the presence of a base to obtain a compound (9):

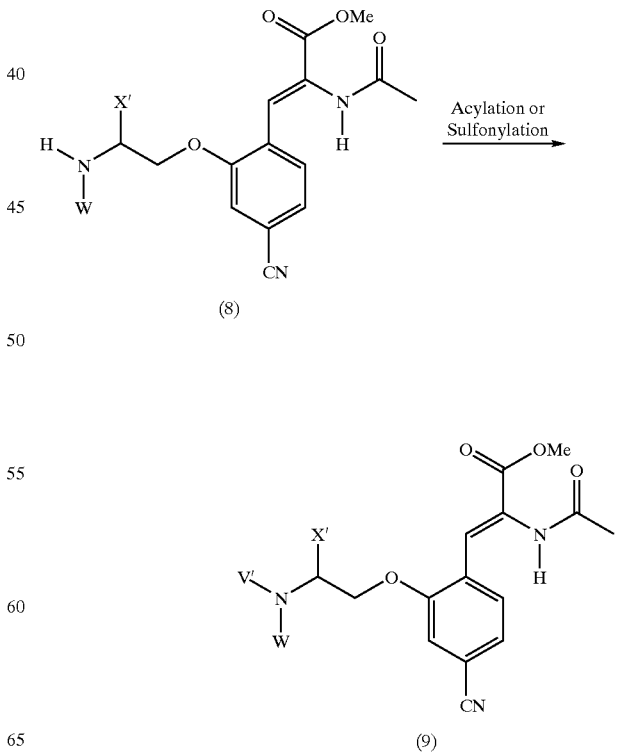

(8)

(9)

wherein V' is the same as V or it represents group V in which the functional group is protected, and W represents hydrogen atom or an alkyl group having 1 to 6 carbon atoms.

Compound (9) can be reacted with an alcohol such as ethanol or methanol in a solvent such as a solution of hydrogen chloride in dioxane to form an imidate, which is then reacted with ammonia gas or an ammonium salt such as ammonium carbonate to form a compound (10) having amidino group derived from cyano group.

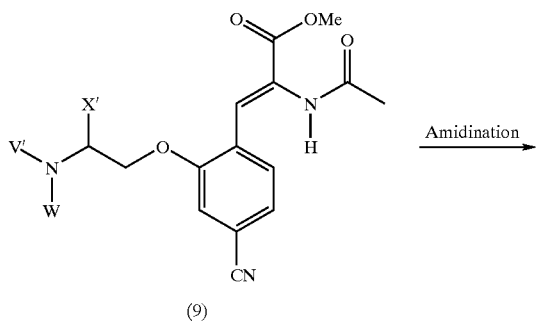

(9)

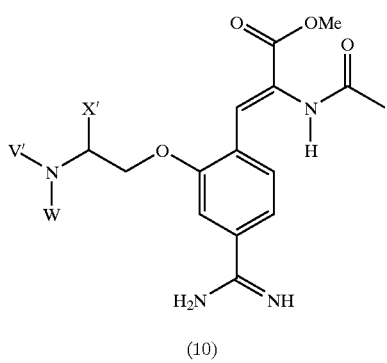

(10)

The obtained amidino compound (10) is hydrolyzed at the ester portion and enamido portion on the 2-alkoxcarbonyl-2-acetamidoethenyl group at the same time to obtain an amidinophenylpyruvic acid derivative (11) of general formula (1) wherein Z represents hydroxyl group and Y represents oxygen atom. If necessary, a step of removing the protecting group from X' or V' is inserted before or after the hydrolysis step.

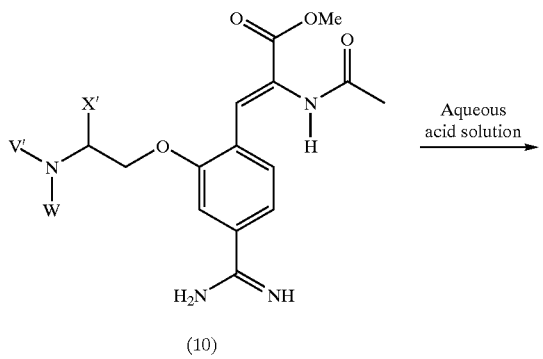

(10)

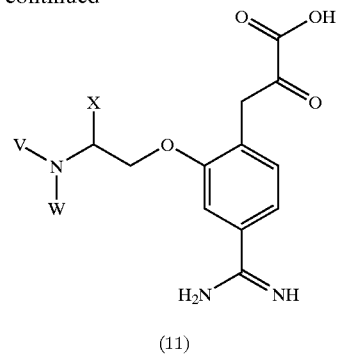

(11)

A compound of general formula (1) wherein Z represents amino group which may have a substituent(s) can be produced by, for example, Mizorogi-Hack reaction to condense an ether compound (5) with 2-acetamidoacrylic acid or the like in the presence of a palladium catalyst or by the selective hydrolysis of the ester part of the acrylic acid ester derivative (6) under an alkaline condition realized by using an aqueous sodium hydroxide solution to obtain the acrylic acid derivative (12).

Then the compound is condensed with an amine such as benzylamine in the presence of a condensing agent such as dicyclohexylcarbodiimide (DCC) to obtain a compound (13) wherein Z represents an amino group which may have a substituent(s). After the removal of the protecting group from nitrogen atom, amidation, or sulfonylation, conversion of amidino group from cyano group or hydrolysis of enamido part in the same manner as that described above, an amidinophenylpyruvic acid derivative of general formula (1) wherein Y represents oxygen atom and Z represents an amino group which may have a substituent(s) can be obtained.

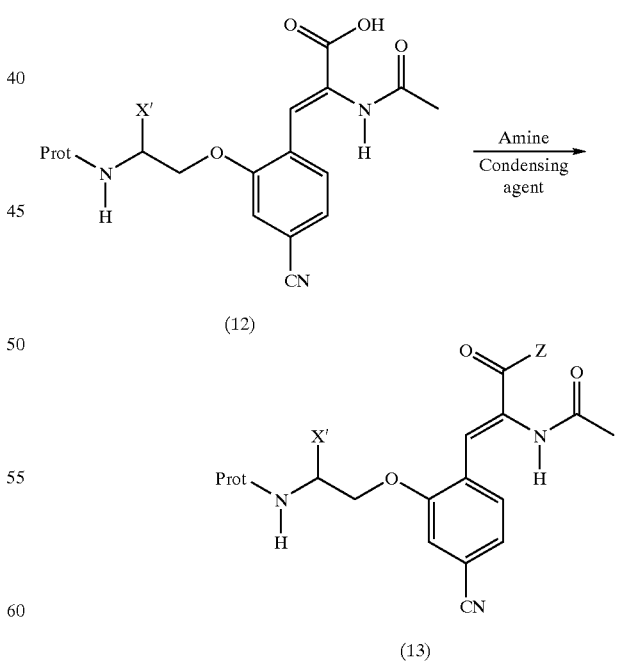

wherein Z represents amino group which may have a substituent(s).

Compounds represented by general formula (1-2) can be also produced in the same manner as that described above.

The compound of general formula (1) or (1-2) thus produced or a salt thereof can be isolated by a well-known purification method such as extraction, concentration, concentration under reduced pressure, extraction with a solvent, crystallization, recrystallization, redissolution or a chromatography.

Evaluation of Antagonistic Activity to Enzymes

Determination of antagonistic activity to activated human blood coagulation factor VII:

100 nM solution of activated human blood coagulation factor VII (Enzyme Research Laboratories Ltd.) in pH 7.4 tris hydrochloride buffer solution was mixed with 100 nM solution of a tissue factor (American Diagnostica Laboratories Ltd.) in pH 7.4 tris hydrochloride buffer solution in equal amounts, and the obtained mixture was left to stand at room temperature for 30 minutes. 50 µl of 50 mM tris hydrochloride buffer solution having a pH adjusted to 7.4 was added to 5 µl of an aqueous solution of a compound to be tested. Then 10 µl of the previously prepared mixture of 50 nM of each of the solutions of activated human blood coagulation factor VII and tissue factor was added to the obtained mixture, and they were incubated at room temperature for 10 minutes. Then 25 µl of 3.2 mM solution of D-isoleucyl-L-prolyl-L-arginyl-P-nitroanilide hydrochloride (S-2288, Daiichi Pure Chemicals Co., Ltd.) in pH 7.4 tris hydrochloride buffer was added to the obtained mixture. The absorbance was determined and the initial reaction velocity was calculated. A control was prepared by using 5 µl of tris hydrochloride buffer adjusted to pH 7.4 in place of the solution of the compound to be tested. The absorbance was determined with MICROPLATE READER Model 3550-UV (BIO RAD) at a wavelength of 405 nm at intervals of 5 minutes for 400 minutes. The negative logarithm ($pIC_{50}$) of the concentration of the sample compound for the 50% inhibition of the activity (initial velocity) of the activated blood coagulation factor VII was determined, and it was employed as the index of the antagonistic activity to the activated blood coagulation factor VII. The antagonistic activities of typical compounds are shown in Table 1 given below.

(2) Determination of Antagonistic Activity to Human Thrombin:

130 µl of 100 mM tris hydrochloride buffer adjusted at pH 8.4 was added to 10 µl of an aqueous solution of a sample compound having antagonistic activity to human thrombin. Then 10 µl of a solution of human thrombin (SIGMA Co. Ltd.) adjusted to 2 units/ml with pH 8.4 tris hydrochloride buffer was added to the obtained mixture, and they were incubated at room temperature for 10 minutes. 50 µl of a 0.4 mM solution of D-phenylalanyl-L-pipecolyl-L-arginyl-P-nitroanilide dihydrochloride (S-2238, Daiichi Pure Chemicals Co., Ltd.) in pH 8.4 tris hydrochloride buffer was added to the obtained mixture. The absorbance was determined and the initial reaction velocity was calculated. A control was prepared by using 10 µl of tris hydrochloride buffer adjusted to pH 8.4 in place of the solution of the compound to be tested. The absorbance was determined with MICROPLATE READER Model 3550-UV (BIO RAD) at a wavelength of 405 nm at intervals of 15 seconds for 6 minutes. The negative logarithm ($pIC_{50}$) of the concentration of the sample compound for the 50% inhibition of the activity (initial velocity) of thrombin was determined, and it was employed as the index of the antagonistic activity to thrombin. The antagonistic activities of typical compounds are shown in Table 1 given below.

TABLE 1

| | Antagonistic activity to activated blood coagulation factor VII ($pIC_{50}$) | Antagonistic activity to thrombin ($pIC_{50}$) |
|---|---|---|
| Compound of Ex. 1 | 6.9 | <4.0 |
| Compound of Ex. 2 | 6.5 | 4.5 |
| Compound of Ex. 4 | 6.7 | <4.0 |
| Compound of Ex. 13 | 7.0 | 5.1 |
| Compound of Ex. 23 | 6.6 | <4.0 |
| Compound of Ex. 27 | 7.3 | . . . |
| Compound of Ex. 28 | 8.3 | <4.0 |
| Compound of Ex. 39 | 7.7 | 4.4 |
| Compound of Ex. 45 | 7.0 | . . . |

Thus, the compounds of the present invention have a high antagonistic activity to activated blood coagulation factor VII, and they are useful as pharmaceutical composition for preventing or treating diseases caused by the blood coagulation, thrombus or embolus, intimal thickening or angiostenosis.

Therefore, the compounds of the present invention are useful as pharmaceutical composition for preventing or treating, for example, disseminated intravascular coagulation, deep vein thrombosis, diseases caused by a pulmonary vascular disorder such as pulmonary embolus or pulmonary infarction, diseases caused by an ischemic heart disease such as acute or chronic myocardial infarction or unstable angina, diseases caused by a cerebrovascular disorder such as transient cerebral ischemic attack (TIA), cerebral thrombosis, cerebral infarction, cerebral embolism, cerebral stroke or vasospasm of patients with subarachnoidal bleeding, occlusion of blood vessel and angiostenosis after coronary artery intervention such as Percutaneous transluminal coronary angioplasty (PTCA) or percutaneous transluminal coronary recanalization (PTCR), formation of thrombi after artificial blood vessel-forming operation or artificial valve replacement, peripheral embolism, formation of thrombi in the course of the extracorporeal circulation and antiphospholipid antibody syndrome. When the compounds of the present invention are used for such a purpose, they exhibit a high selectivity toward other enzymes and undesirable side effects such as hemorrhage of patients with serious illness can be advantageously inhibited. Further, since the compounds of the present invention are organic compounds having low molecular weights, they are highly soluble and usable in various dosage forms. The administration routes of them can be selected in a wide range such as intravenous injection and oral administration. The compounds of the present invention are highly stable in blood and very useful.

For the purposes described above, the compounds of the present invention are administered as they are or in the forms of various pharmaceutical compositions. The administration routes of them are, for example, oral administration, parenteral administration such as intravenous, subcutaneous or intramuscular administration, percutaneous administration and rectal administration. The dosage forms of the medicinal compositions are, for example, tablets, suppositories, pills, capsules, powders, suspensions, aerosols, liquids, injections, syrups and emulsions. These medicinal compositions can be prepared by an ordinary preparation method. They comprise a compound of the present invention as the active ingredient and a well-known excipient or carrier and, they contain, if necessary, an adjuvant, additives, etc. For tablets, for example, the adjuvants are inert diluents such as lactose, calcium carbonate and calcium phosphate; the adjuvants are binders such as acacia, corn starch and gelatin, and lubricants such as magnesium stearate, talc and carboxymethyl cellulose; and the additives are sweetening agents such as sucrose, lactose and saccharin, and corrigents such as peppermint and cherry.

The dose of the compounds of the present invention as the anticoagulants varies depending on the administration method, age, body weight and condition of the patient to be treated. The dose is usually 0.01 to 1,000 mg, preferably 0.1 to 50 mg, a day for adults in the oral administration, and 1 μg to 100 mg, preferably 0.01 to 10 mg, a day for adults in the parenteral administration.

The following Examples and Referential Examples will further illustrate the present invention, which by no means limit the invention.

In the following Examples, NMR spectrum of each of the compounds of general formula (1) wherein Z represents hydroxyl group and those of general formula (1-2) in DMSO-d6 was a mixture of compounds of keto- and enol types.

Referential Example 1

Methyl 2-acetamido-3-[2-(2-aminoethoxy)-4-cyanophenyl] acrylate hydrochloride:

Step 1
3-Hydroxy-4-iodobenzoic acid:

30.0 g (217 mmol) of 3-hydroxybenzoic acid was dissolved in 200 ml of acetic acid. 53.0 g (326 mmol) of iodine monochloride was added to the obtained solution at room temperature. They were stirred at 45° C. for 15 hours and then the solvent was evaporated under reduced pressure. The residue was washed with 500 ml of 1% aqueous sodium thiosulfate solution twice and with 500 ml of water twice and then dried to solid at 80° C. under reduced pressure to obtain the title compound.

Yield: 17.2 g (65.2 mmol) (30%)
MS (FAB, m/z) 265 (MH+)
H-NMR (DMSO-6) δ7.13 (1H, dd), 7.43 (1H, d), 7.80 (1H, d)

Step 2
3-Hydroxy-4-iodobenzonitrile:

19.7 ml (206 mmol) of ethyl chloroformate and 28.7 ml (206 mmol) of triethylamine were added to a solution of 22.3 g (89.7 mmol) of 3-hydroxy-4-iodobenzoic acid in 300 ml of tetrahydrofuran at 0° C. After stirring for 15 minutes, triethylamine hydrochloride thus formed was filtered off. The filtrate was added to 300 ml of tetrahydrofuran solution, obtained by bubbling ammonia, at 0° C. They were stirred at room temperature for 10 hours and the solvent was evaporated under reduced pressure. The residue was dissolved in 450 ml of dioxane. 17.4 ml (117 mmol) of trifluoroacetic acid anhydride and 21.8 ml (269 mmol) of pyridine were added to the obtained solution at 0° C. After stirring at room temperature for 18 hours, the solvent was evaporated under reduced pressure. The residue was treated with chloroform as an extracting solvent by an ordinary method to obtain an oily residue. The residue was dissolved in 180 ml of tetrahydrofuran/methanol (1/1). 90 ml (90.0 mmol) of 1 N aqueous sodium hydroxide solution was added to the obtained solution at room temperature. They were stirred for 4 hours, and the solvent was evaporated under reduced pressure. The residue was washed with dichloromethane. The product was acidified with 1 N hydrochloric acid and then treated with ethyl acetate as the extracting solvent by an ordinary method to obtain a crude product, which was purified by the silica gel column chromatography to obtain the title compound.

Yield: 9.29 g (37.9 mmol) (42%)
MS (FAB, m/z) 246 (MH+)
H-NMR (CDCl13) δ5.63 (1H, br), 6.96 (1H, dd), 7.23 (1H, d), 7.79 (1H, d)

Step 3
t-Butyl(2-bromoethyl) carbamate:

9.22 g (45 mmol) of 2-bromoethylamine hydrobromide was dissolved in 100 ml of dichloromethane. 7.64 g (35 mmol) of di-t-butyl dicarbonate, 10.0 g (99 mmol) of triethylamine and 100 mg (0.82 mmol) of 4-(dimethylamino)pyridine were added to the obtained solution, and they were stirred overnight. After the treatment with dichloromethane as the extracting solvent by an ordinary method, the title compound was obtained.

Yield: 5.99 g (26.7 mmol) (76%)
H-NMR (CDCl 3) δ 1.45 (9H, s), 3.46 (2H, dt), 3.51 (2H, t), 4.95 (1H, br)

Step 4
3-[2-(t-Butoxycarbonylamino)ethoxy]-4-iodobenzonitrile:

18.5 g (82.6 mmol) of t-butyl(2-bromoethyl) carbamate was dissolved in 200 ml of dimethylformamide (DMF). 10.1 g (41.3 mmol) of 3-hydroxy-4-iodobenzonitrile and 5.7 g (41.3 mmol) of potassium carbonate were added to the obtained solution, and they were stirred at 75° C. for 3 hours. After the treatment with ethyl acetate as the extracting solvent by an ordinary method, the title compound was obtained.

Yield: 11.0 g (28.4 mmol) (69%)
H-NMR (CDCl 3) δ 1.46 (9H, s), 3.62 (2H, dt), 4.12 (2H, t), 7.02 (2H, d), 7.88 (2H, d).

Step 5
Methyl 2-acetamido-3-[2-(2-(t-butoxycarbonylamino) ethoxy)-4-cyanophenyl]acrylate:

18.0 g (46.4 mmol) of 3-[2-(t-butoxycarbonylamino) ethoxy]-4-iodobenzonitrile was dissolved in 200 ml of dimethylformamide (DMF). 13.3 g (92.8 mmol) of methyl 2-acetamidoacrylate, 2.82 g (9.28 mmol) of tris(2-methylphenyl)phosphine, 1.04 g (4.64 mmol) of palladium (II) acetate and 12.9 ml (92.8 mmol) of triethylamine were added to the obtained solution, and they were stirred at 115° C. for 4 hours. The solvent was evaporated to obtain the crude product, which was purified by the silica gel column chromatography to obtain the title compound.

Yield: 12.2 g (30.3 mmol) (65%)
H-NMR (CDCl3) δ1.45 (9H, s), 2.03 (3H, s), 3.58 (2H, dt), 3.89 (3H, s), 4.18 (2H, t), 7.17 (1H, br), 7.23 (1H, d), 7.35–7.42 (2H, m)
H-NMR (DMSO-d6) δ1.38 (9H, s), 1.95 (3H, s), 3.35 (2H, dt), 3.70 (3H, s), 4.10 (2H, t), 7.03 (1H, t), 7.20 (1H, s), 7.43 (1H, d), 7.55 (1H, s), 7.68 (1H, d), 9.65 (1H, s)

Step 6
Methyl 2-acetamido-3-[2-(2-aminoethoxy)-4-cyanophenyl] acrylate hydrochloride:

30 ml of dioxane was added to 7.75 g (19.2 mmol) of methyl 2-acetamido-3-[2-(2-t-butoxycarbonylaminoethoxy)-4-cyanophenyl]-acrylate, and they were stirred. 80 ml of dioxane containing 4 M of hydrogen chloride was added to the obtained mixture, and they were stirred at room temperature for 1 hour. The solvent was evaporated, and the residue was suspended in ethyl acetate. The title compound was obtained by the filtration.

Yield: 4.38 g (12.9 mmol) (67%)
H-NMR (DMSO-d6) δ1.95 (3H, s), 3.25 (2H,dt), 3.70 (3H, s), 4.30 (2H, t), 7.28 (1H,s), 7.48 (1H, d), 7.62 (1H, s), 7.70 (1H, d), 8.20 (3H,br), 9.75 (1H, s)

Referential Example 2

Methyl 2-acetamido-3-[2-[(2R)-2-amino-4-benzyloxycarbonylbutoxy]-4-cyano-phenyl]acrylate hydrochloride:

Step 1
Benzyl (4R)-4-t-butoxycarbonylamino-5-hydroxypentanoate:

10.9 g (32 mmol) of γ-benzyl N-t-butoxycarbonyl-D-glutamate and 3.29 g (32.5 mmol) of N-methylmorpholine were stirred in 100 ml of tetrahydrofuran. 3.08 ml (32 mmol) of ethyl chloroformate was added to the obtained mixture under cooling with ice, and they were stirred. A precipitate thus formed was filtered out. Ice and 1.23 g (32.5 mmol) of sodium borohydride were added to the filtrate, and they were stirred for 3 minutes. Water and 1 M of hydrochloric acid were added to the reaction mixture, and they were stirred for 1 hour. After the extraction with ethyl acetate, the extract was washed with saturated aqueous sodium hydrogencarbonate solution and saturated aqueous sodium chloride solution and then dried over anhydrous magnesium sulfate. The solvent was evaporated to obtain the title compound.

Yield: 10.9 g

H-NMR (CDCl3) δ1.45 (9H, s), 1.75–2.00 (2H, m), 2.40–2.50 (2H, m), 3.50–3.70 (3H, m), 4.80 (1H, br), 5.10 (2H, s), 7.35 (5H, s)

Step 2
Benzyl (4R)-4-t-butoxycarbonylamino-5-chloropentanoate:

10.8 g (33.4 mmol) of benzyl (4R)-4-t-butoxycarbonylamino-5-hydroxypentanoate and 3.4 g (33.4 mmol) of triethylamine were stirred in 200 ml of dichloromethane. 3.83 g (33.4 mmol) of methanesulfonyl chloride was added to the obtained mixture under cooling with ice. Crude benzyl (4R)-4-t-butoxycarbonylamino-5-methanesulfonyloxypentanoate was obtained by an ordinary method with dichloromethane as the extracting solvent. The crude product was stirred together with 7.2 g (170 mmol) of lithium chloride in 50 ml of DMF at 50° C. overnight. The solvent was evaporated, and the crude title compound obtained by an ordinary method with ethyl acetate as the extracting solvent was washed with a solvent mixture of hexane and ethyl acetate to obtain the title compound.

Yield: 8.29 g

H-NMR (CDCl3) δ1.40 (9H, s), 1.90–2.00 (2H, m), 2.40–2.50 (2H, m), 3.55–3.70 (2H, m), 3.85–4.00 (1H, m), 4.70 (1H, br), 5.10 (2H, s), 7.35 (5H, s)

Step 3
Benzyl (4R)-4-t-butoxycarbonylamino-5-(5-cyano-2-iodophenoxy)pentanoate:

8.29 g (24.3 mmol) of benzyl (4R)-4-t-butoxycarbonylamino-5-chloropentanoate, 6.9 g (28.0 mmol) of 3-hydroxy-4-iodobenzonitrile, 6.9 g (50 mmol) of potassium carbonate and 4.15 g (25 mmol) of potassium iodide were stirred together in 80 ml of DMF at 70° C. for 3 days. The solvent was evaporated, and the crude product obtained by an ordinary method with ethyl acetate as the extracting solvent was purified by the silica gel chromatography (ethyl acetate/hexane) to obtain the title compound.

Yield: 5.72 g

H-NMR (CDCl3) δ1.45 (9H, s), 2.10 (2H, br), 2.55 (2H, t), 4.05 (3H, br), 4.90 (1H, br), 5.15 (2H, s), 6.95 (1H, s), 7.00 (1H, d), 7.35 (5H, s), 7.90 (1H, d)

Step 4
Methyl 2-acetamido-3-[2-[(2R)-4-benzyloxycarbonyl-2-(t-butoxycarbonylamino)butoxy]-4-cyanophenyl]acrylate:

5.72 g (10.4 mmol) of benzyl (4R)-4-t-butoxycarbonylamino-5-(5-cyano-2-iodophenoxy)pentanoate was stirred together with 3.0 g (21 mmol) of methyl 2-acetamidoacrylate, 2.0 g (6.6 mmol) of tris(2-methylphenyl)phosphine, 270 mg (1.1 mmol) of palladium (II) acetate and 3.54 g (35 mmol) of triethylamine in 50 ml of DMF at 100° C. for 5 hours. The solvent was evaporated, and the residue was treated with ethyl acetate as the extracting solvent by an ordinary method and then purified by the silica gel chromatography (ethyl acetate/hexane) to obtain the title compound.

Yield: 2.6 g

H-NMR (CDCl3) δ1.40 (9H, s), 1.80–2.05 (2H, m), 2.05 (3H, br), 2.50 (2H, t), 3.85 (3H, s), 4.05 (3H, br), 4.85 (1H, d), 5.10 (2H, s), 7.12 (1H, s), 7.23 (1H, d), 7.31–7.48 (8H, m)

Step 5
Methyl 2-acetamido-3-[2-[(2R)-4-benzyloxycarbonyl-2-aminobutoxy]-4-cyanophenyl]acrylate hydrochloride:

5 g of methyl 2-acetamido-3-[2-[(2R)-4-benzyloxycarbonyl-2-(t-butoxycarbonylamino)butoxy]-4-cyanophenyl]acrylate was stirred in 50 ml of dioxane containing 4 M of hydrogen chloride for 2 hours. The solvent was evaporated to obtain the title compound.

Yield: 4.5 g

H-NMR (DMSO-d6) δ1.90–2.10 (5H, m), 2.65 (2H, t), 3.60 (1H, br), 3.70 (3H, s), 4.15–4.35 (2H, m), 5.10 (2H, s), 7.30 (1H, s), 7.35 (5H, s), 7.48 (1H, d), 7.60 (1H, s), 7.70 (1H, d), 8.40 (3H, br), 9.75 (1H,s)

EXAMPLE 1

(4R)-4-[(2-Aminoquinoline-6-carbonyl)amino]-5-[5-amidino-2-(2-carboxy-2-oxoethyl)phenoxy]pentanoic acid bistrifluoroacetate:

Step 1
Ethyl quinoline-6-carboxylate:

4.9 g of quinoline-6-carboxylic acid was stirred in 80 ml of ethanol. 40 ml of dioxane containing 4 M of hydrogen chloride was added to the obtained mixture. After stirring at 70° C. overnight, the solvent was evaporated and the residue was treated with ethyl acetate as the extracting solvent by an ordinary method to obtain the title compound.

Yield: 5.8 g

H-NMR (CDCl3) δ1.45 (3H, t), 4.45 (2H, q), 7.45 (1H, dd), 8.15 (1H, d), 8.25–8.35 (2H, m), 8.60 (1H, s), 9.00 (1H, d)

Step 2
Ethyl 2-chloroquinoline-6-carboxylate:

5.8 g (29 mmol) of ethyl quinoline-6-carboxylate was stirred in 80 ml of dichloromethane. 6.2 g of m-chloroperbenzoic acid was added to the obtained mixture under cooling with ice, and they were stirred at room temperature overnight. The mixture was washed with 10% aqueous sodium sulfite solution, saturated aqueous sodium hydrogencarbonate solution and saturated aqueous sodium chloride solution, and then dried over anhydrous magnesium sulfate. The solvent was evaporated. 70 ml of dichloromethane and 35 ml of phosphoryl chloride were added to the residue, and they were stirred at 50° C. overnight. The solvent was evaporated, and the residue was treated with dichloromethane as the extracting solvent by an ordinary method. After the purification by the silica gel chromatography (ethyl acetate/hexane), the title compound was obtained.

Yield: 1.87 g

H-NMR (CDCl3) δ1.40 (3H, t), 4.45 (2H, d), 7.46 (1H, d), 8.06 (1H, d), 8.21 (1H, d), 8.34 (1H, d), 8.58 (1H, s)

Step 3
Ethyl 2-aminoquinoline-6-carboxylate:

1.87 g (8 mmol) of ethyl 2-chloroquinoine-6-carboxylate and 5.5 g of phenol were stirred together at 70° C. for 10 minutes. 5.5 g of ammonium acetate was added to the obtained mixture, and they were stirred for additional 1 hour. After the treatment with ethyl acetate as the extracting solvent by an ordinary method, the obtained residue was purified by the silica gel chromatography (hexane/ethyl acetate/ethanol) to obtain the title compound.

Yield: 330 mg

H-NMR (CDCl3) δ1.40 (3H, t), 4.40 (2H, q), 5.00 (2H, br), 6.75 (1H, d), 7.64 (1H, d), 7.95 (1H, d), 8.16 (1H, d), 8.37 (1H, s)

Step 4

2-Aminoquinoline-6-carboxylic acid hydrochloride:

330 mg of ethyl 2-aminoquinoline-6-carboxylate was stirred in 30 ml of 6 M hydrochloric acid at 80° C. overnight. The solvent was evaporated, and the residue was washed with ethyl acetate to obtain the title compound.

Yield: 330 mg

H-NMR (DMSO-d6) δ7.16 (1H, d), 7.78 (1H, d), 8.23 (1H, d), 8.50 (1H, d), 8.55 (1H, s)

Step 5

Methyl 2-acetamido-3-[2-[(2R)-2-[2-aminoquinoline-6-carbonylamino]-4-benzyloxycarbonylbutoxy]-4-cyanophenyl]acrylate trifluoroacetate:

A mixture of 210 mg of 2-aminoquinoline-6-carboxylic acid hydrochloride, 520 mg of methyl 2-acetamido-3-[2-[(2R)-2-amino-4-benzyloxycarbonylbutoxy]-4-cyanophenyl]acrylate hydrochloride, 135 mg of 1-hydroxybenzotriazole, 211 mg of 1-[3-(dimethylamino)propyl]-3-ethylcarbodiimide hydrochloride (WSC.HCl), 300 mg of triethylamine and 10 ml of dimethylformamide was stirred at room temperature overnight.

The solvent was evaporated, and the residue was subjected to the reversed-phase high-performance liquid chromatography (reversed phase HPLC) with silica gel of chemically bonded octadodecyl group type as the packing material, and then to the elution with a solvent mixture of water and acetonitrile containing 0.1% (v/v) of trifluoroacetic acid. The fraction of the intended product was freeze-dried to obtain the title compound.

Yield: 140 mg

MS (ESI,m/z) 636(MH+)

H-NMR (DMSO-d6) δ1.90–2.10 (5H, m), 2.55 (2H, t), 3.55 (3H, s), 4.10–4.35 (2H, ,m), 4.45 (1H, br), 5.05 (2H, s), 7.11 (1H, d), 7.17 (1H, s), 7.34 (5H, s), 7.42 (1H, d), 7.65–7.72 (3H, m), 8.14 (1H, dd), 8.36 (1H, s), 8.37 (1H, d), 8.57 (1H, d), 9.65 (1H, s)

Step 6

(4R)-4-[(2-Aminoquinoline-6-carbonyl)amino]-5-[5-amidino-2-(2-carboxy-2-oxoethyl)phenoxy]pentanoic acid bistrifluoroacetate:

A mixture of 140 mg of methyl 2-acetamido-3-[2-[(2R)-2-(2-aminoquinoline-6-carbonylamino)-4-benzyloxycarbonylbutoxy]-4-cyano-phenyl]acrylate trifluoroacetate, 1 ml of ethanol and 10 ml of dioxane containing 4 M of hydrogen chloride was stirred for 2 days. The solvent was evaporated. 15 ml of ethanol and 140 mg of ammonium carbonate were added to the residue, and they were stirred overnight. The solvent was evaporated. 4 M hydrochloric acid was added to the residue, and they were stirred at 80° C. for 1.5 hours. The solvent was evaporated, and the residue was purified by the reversed-phase high-performance liquid chromatography to obtain the title compound in the same manner as that in step 5 in Example 1.

Yield: 63 mg

MS (ESI,m/z) 508 (MH+) MS (ESI,m/z) 506 (MH−)

H-NMR (DMSO-d6) δ1.80–2.10 (2H, m), 2.30–2.50 (2H, m), 4.10–4.30 (2H+keto 2H, m), 4.45 (1H, br), 6.75 (enolic1H, s), 7.10 (1H, d), 7.35–7.50 (2H+keto 1H, m), 7.65 (1H, d), 8.15 (1H, d), 8.25–8.45 (2H+enol 1H), 8.65 (1H, d), 8.90 (2H, br), 9.10 (2H, br), 9.25 (2H, br)

EXAMPLE 2

3-[4-Amidino-2-[2-(2-aminoquinoline-6-carbonyl)aminoethoxy]phenyl]-2-oxopropionic acid bistrifluoroacetate:

2-Aminoquinoline-6-carboxylic acid hydrochloride was used as the starting material. A condensate of this compound with methyl 2-acetamido-3-[2-(2-aminoethoxy)-4-cyanophenyl]acrylate hydrochloride was produced in the same manner as that in step 5 in Example 1, and then treated in the same manner as that in step 6 in Example 1 to obtain the title compound.

MS (ESI,m/z) 436 (MH+) MS (ESI,m/z) 434(MH−)

H-NMR(DMSO-d6) δ3.60–3.80 (2H, m), 4.10–4.40 (2H+keto 2H, m), 6.80 (enol 1H,s), 7.10 (1H, d), 7.35–7.54 (2H+keto 1H, m), 7.70 (1H, d), 8.15 (1H, d), 8.30–8.44 (2H+enol 1H, m), 8.97 (1H, br), 9.05 (2H, br), 9.30 (2H, br)

EXAMPLE 3

(4R)-4-[(2-Aminobenzimidazole-5-carbonyl)amino]-5-[5-amidino-2-(2-carboxy-2-oxoethyl)phenoxy]pentanoic acid bistrifluoroacetate:

Step 1:

Methyl 2-aminobenzimidazole-5-carboxylate:

300 mg (1.8 mmol) of methyl 3,4-diaminobenzoate was stirred in 5 ml of water. 0.5 ml of a solution of 5 M of cyanogen bromide in acetonitrile was added to the obtained mixture, and they were stirred at room temperature for 20 minutes. The mixture was filtered. Aqueous ammonia was added to the filtrate. After the treatment with ethyl acetate as the extracting solvent by an ordinary method, the title compound was obtained.

Yield: 320 mg

H-NMR (DMSO-d6) δ3.80 (3H, s), 6.50 (2H, br), 7.15 (1H, d), 7.55 (1H, d), 7.70 (1H, s), 10.90 (1H, br)

Step 2:

2-Aminobenzimidazole-5-carboxylic acid hydrochloride:

320 mg of methyl 2-aminobenzimidazole-5-carboxylate was stirred in 3 M of hydrochloric acid at 65° C. overnight, and the solvent was evaporated to obtain the title compound.

Yield: 330 mg

H-NMR (DMSO-d6) δ7.45 (1H, d), 7.85 (1H, d), 7.95 (1H, s), 8.80 (2H, s), 13.00 (1H, br)

Step 3

(4R)-4-[(2-Aminobenzimidazole-5-carbonyl)amino]-5-[5-amidino-2-(2-carboxy-2-oxoethyl)phenoxy]pentanoic acid bistrifluoroacetate:

The title compound was obtained from 2-aminobenzimidazole-5-carboxylic acid hydrochloride as the starting material in the same manner as that in steps 5 and 6 in Example 1.

MS (ESI,m/z) 497(MH+) 495(MH−)

H-NMR(DMSO-d6) δ1.80–2.15(2H,m), 2.25–2.50(2H, m), 4.05–4.50 (3H+keto 2H,m), 6.80 (enol 1H,s), 7.35–7.50 (3H+keto 1H,m), 7.75(1H,d), 7.80(1H,s), 8.30(enol 1H,d), 8.45(1H,d), 8.65(2H,s), 9.10(2H,s), 9.25(2H,s)

EXAMPLE 4

(4R)-4-[(2-Methylbenzimidazole-5-carbonyl)amino]-5-[5-amidino-2-(2-carboxy-2-oxoethyl)phenoxy]pentanoic acid bistrifluoroacetate The title compound was obtained from 2-methylbenzimidazole-5-carboxylic acid as the starting material in the same manner as that in steps 5 and 6 in Example 1.

MS (ESI,m/z) 496(MH+) 494(MH−)

H-NMR(DMSO-d6) δ1.85–2.15 (2H, m), 2.25–2.50 (2H, m), 2.75 (3H, s), 4.10–4.30 (2H+keto 2H, m), 4.45 (1H, br), 6.80 (enol 1H, s), 7.35–7.55 (2H+keto 1H, m), 7.73 (1H, d), 7.87–7.96 (1H, m), 8.16 (1H, s), 8.32 (enol 1H,d), 8.49–8.64 (1H,m), 9.10 (2H, br), 9.30 (2H, br)

EXAMPLE 5

3-[4-Amidino-2-[2-(2-methylbenzimidazole-5-carbonyl) aminoethoxy]-phenyl]-2-oxopropionic acid bistrifluroacetate:

2-Methylbenzimidazole-5-carboxylic acid was used as the starting material. A condensate of this compound with methyl 2-acetamido-3-[2-(2-aminoethoxy)-4-cyanophenyl] acrylate hydrochloride was produced in the same manner as that in step 5 in Example 1, and then treated in the same manner as that in step 6 in Example 1 to obtain the title compound.

MS (ESI,m/z) 424(MH+) 422(MH−)

H-NMR(DMSO-d6) δ2.75(3H,s), 3.60–3.80(2H,m), 4.15–4.35(2H+keto 2H, m), 6.80(enol 1H,s), 7.40–7.50 (2H+keto 1H,m), 7.75(1H,d), 7.95(1H,d), 8.20(1H,s), 8.35 (enol 1H,d), 8.80–9.00(1H,m), 9.10(2H,s), 9.30(2H,s)

EXAMPLE 6

(4R)-4-[(Benzimidazole-5-carbonyl)amino]-5-[5-amidino-2-(2-carboxy-2-oxoethyl)phenoxy]pentanoic acid bistrifluoroacetate:

The title compound was obtained from benzimidazole-5-carboxylic acid as the starting material in the same manner as that in steps 5 and 6 in Example 1.

MS (ESI,m/z) 482(MH+) 480(MH−)

H-NMR(DMSO-d6) δ1.80–2.15 (2H, m), 2.15–2.80 (2H, m), 4.00–4.30 (2H+keto 2H, m), 4.45 (1H, br), 6.80 (1H, s), 7.35–7.55 (2H+keto 1H, m), 7.70 (1H, d), 7.86 (1H,d), 8.20 (1H, s), 8.32 (enol 1H, d), 8.52 (1H, d), 8.77 (1H, s), 9.00 (2H, br), 9.28 (2H, br)

EXAMPLE 7

(4R)-4-[(5-Guanidinothiophene-2-carbonyl)amino]-5-[5-amidino-2-(2-carboxy-2-oxoethyl)phenoxy]pentanoic acid bistrifluoroacetate:

Step 1

Synthesis of chloroformamidine hydrochloride:

1.4 g of cyanamide was dissolved in 20 ml of dioxane. 30 ml of dioxane containing 4 M of hydrogen chloride was added to the obtained solution, and they were stirred at room temperature. A precipitate thus formed was taken by the filtration and dried in vacuo to obtain the title compound.

Yield: 3.0 g

Step 2

Ethyl 5-nitrothiophene-2-carboxylate:

5 g of 5-nitrothiophene-2-carboxylic acid was stirred in 100 ml of ethanol. 20 ml of dioxane containing 4 M of hydrogen chloride was added to the obtained mixture, and they were stirred at 60° C. for 2 days. The solvent was evaporated to obtain the title compound.

Yield: 5.5 g

H-NMR(CDCl3) δ1.40 (3H, t), 4.40 (2H, q), 7.70 (1H, d), 7.90 (1H, d)

Step 3

Ethyl 5-guanidinothiophene-2-carboxylate trifluoroacetate:

1.9 g (9.4 mmol) of ethyl 5-nitrothiophene-2-carboxylate and 500 mg of 10% palladium/carbon (50% hydrous) were stirred in ethanol in hydrogen atmosphere for 3 days. The reaction mixture was filtered, and the filtrate was concentrated. 10 g of dimethyl sulfone and 3.0 g of chloroformamidine hydrochloride were added to the residue, and they were heated at 120° C. for 30 minutes. 1 M of hydrochloric acid was added to the reaction mixture. After washing with ethyl acetate, the aqueous layer was concentrated, and the obtained residue was purified by the reversed-phase HPLC in the same manner as that in step 5 in Example 1 to obtain the title compound.

Yield: 1.0 g

H-NMR(DMSO-d6) δ1.25 (3H, t), 4.30 (2H, q), 7.00 (1H, d), 7.65 (1H, d), 7.80 (4H, br), 10.70 (1H, s)

Step 4

5-Guanidinothiophene-2-carboxylic acid hydrochloride:

1 g of ethyl 5-guanidinothiophene-2-carbxylate trifluoroacetate was stirred in 50 ml of ethanol. 20 ml of aqueous solution of 1 M of sodium hydroxide was added to the obtained mixture. After stirring at room temperature overnight, the reaction mixture was neutralized with 1 M of hydrochloric acid and then concentrated. The residue was purified by the reversed-phase HPLC in the same manner as that in step 5 in Example 1 to obtain 5-guanidinothiophene-2-carboxylic acid Trifluoroacetate. 1 M of hydrochloric acid was added to this product and they were freeze-dried to obtain the title compound.

H-NMR(DMSO-d6) δ7.00 (1H, d), 7.60 (1H, d), 7.90 (4H, br), 10.60 (1H, br)

Step 5

(4R)-4-[(5-Guanidinothiophene-2-carbonyl)amino]-5-[5-amidino-2-(2-carboxy-2-oxoethyl)phenoxy]pentanoic acid bistrifluoroacetate:

The title compound was obtained from 5-guanidinothiophene-2-carboxylic acid hydrochloride as the starting material in the same manner as that in Steps 5 and 6 in Example 1.

MS (ESI,m/z) 505(MH+) 503(MH−)

H-NMR(DMSO-d6) δ1.80–2.10 (2H, m), 2.25–2.50 (2H, m), 4.00–4.40 (3H+keto 2H, m), 6.80 (enol 1H, s), 6.95 (1H, d), 7.30–7.50 (2H+keto 1H, m), 7.70 (4H, br), 7.75 (1H, d), 8.33 (enol 1H, d), 8.52 (1H, d), 9.05 (2H, br), 9.25 (2H, br), 10.20 (1H, br)

EXAMPLE 8

(4R)-4-[(4-Guanidinonaphthalene-1-carbonyl)amino]-5-[5-amidino-2-(2-carboxy-2-oxoethyl)phenoxy]pentanoic acid bistrifluoroacetate:

Step 1

4-Amino-1-naphthalenecarboxylic acid:

1.60 g (2.3 mmol) of bis(triphenylphosphine) dichloropalladium, 7.0 ml (50.6 mmol) of triethylamine and 60 ml of methanol were successively added to a mixture of 5.00 g (22.5 mmol) of 1-amino-4-bromonaphthalene and 60 ml of dimethylformamide, and they were stirred in carbon monoxide atmosphere at 80° C. for 2 days. After the concentration under reduced pressure, water was added to the reaction mixture and the product was extracted with ethyl acetate and concentrated. 20 ml of ethanol and 10 ml (40.0 mmol) of 4 N aqueous sodium hydroxide solution were added to crude methyl 4-amino-1-naphthalenecarboxylate thus obtained. They were stirred at 80° C. overnight. Ethanol was evaporated, and the residue was washed with ethyl acetate. The aqueous layer was neutralized with hydrochloric acid. After the extraction with ethyl acetate, the product was washed with water and saturated aqueous sodium chloride solution, dried over anhydrous sodium sulfate and concentrated under reduced pressure to obtain the title compound.

Yield: 1.85 g

MS (ESI,m/z) 194(M+H)+

H-NMR(DMSO-d6) δ6.61–6.68(3H,m), 7.40(1H,t), 7.54 (1H,t), 8.05(1H,d), 8.15(1H,d), 9.12(1H,d), 12.00–12.15 (1H,brs)

Step 2
4-Guanidino-1-naphthalenecarboxylic acid trifluoroacetate:

A mixture of 1.40 g (7.5 mmol) of 4-amino-1-naphthalenecarboxylic acid and 150 ml of dioxane containing 4 M of hydrogen chloride was stirred at room temperature for 30 minutes. Then the solvent was evaporated. 100 ml of ethanol, 7.10 g of cyanamide and 100 mg of concentrated hydrochloric acid were added to the residue, and they were stirred at 60° C. for 2 days. After the concentration under reduced pressure, the residue was purified by the reversed-phase HPLC in the same manner as that in step 5 in Example 1 to obtain the title compound.

Yield: 70 mg
MS (ESI,m/z) 230(M+H)+
H-NMR(DMSO-d6) δ7.48–7.62(5H,m),7.68–7.78(2H,m),8.00–8.09(1H,m), 8.18(1H,d),8.92–8.97(1H,m), 10.15–10.33(1H,m)

Step 3
(4R)-4-[(4-guanidinonaphthalene-1-carbonyl)amino]-5-[5-amidino-2-(2-carboxy-2-oxoethyl)phenoxy]pentanoic acid bistrifluoroacetate:

The title compound was obtained from 4-guanidino-1-naphthalenecarboxylic acid trifluoroacetate in the same manner as that in steps 5 and 6 in Example 1.

MS (ESI,m/z) 549(M+H)+
H-NMR(DMSO-d6) δ1.80–2.10 (2H, m), 2.36–2.45 (2H, m), 4.00–4.40 (2H+keto 2H, m), 4.42–4.62 (1H, m), 6.91 (enol 1H, s), 7.35–7.70 (10H+keto 1H, m), 7.94 (1H, d), 8.25–8.40(1H+enol 1H, m), 8.64(1H, d), 9.10 (2H, s), 9.28 (2H, s), 10.17 (1H, s)

EXAMPLE 9
(4R)-4-[(3-Guanidinomethylbenzoyl)amino]-5-[5-amidino-2-(2-carboxy-2-oxoethyl)phenoxy]pentanoic acid bistrifluoroacetate:

Step 1
3-Guanidinomethylbenzoic acid trifluoroacetate:

4.34 g (20.0 mmol) of di(t-butyl) iminodicarboxylate was added to a mixture of 800 mg (20.0 mmol) of sodium hydride (60% dispersion in mineral oil) and 50 ml of dimethylformamide. 1.71 g (10.0 mmol) of 3-chloromethylbenzoic acid was added to the obtained mixture, and they were stirred at 80° C. for 2 hours. After the concentration under reduced pressure, 40 ml of dioxane containing 4 M of hydrogen chloride was added to the residue, and they were stirred at room temperature overnight. A white precipitate thus formed was taken by the filtration and washed with ethyl acetate to obtain 3-aminomethylbenzoic acid hydrochloride as white crystals. A mixture of this aminomethyl compound, 10 ml of water, 10 ml of 28% aqueous ammonia and 3.00 g (71.4 mmol) of cyanamide was stirred at 60° C. for 7 days. The solvent was evaporated, and the residue was purified by the reversed-phase HPLC in the same manner as that in step 5 in Example 1 to obtain the title compound.

Yield: 80 mg
MS (ESI,m/z) 194(M+H)+
H-NMR(DMSO-d6) δ4.45(2H,d), 7.10–7.40(4H,brs), 7.50–7.58(2H,m), 7.84–8.10(3H,m)

Step 2
(4R)-4-[(3-Guanidinomethylbenzoyl)amino]-5-[5-amidino-2-(2-carboxy-2-oxoethyl)phenoxy]pentanoic acid bistrifluoroacetate:

The title compound was obtained from 3-guanidinomethylbenzoic acid trifluoroacetate in the same manner as that in steps 5 and 6 in Example 1.

MS (ESI,m/z) 513(M+H)+
H-NMR(DMSO-d6) δ1.80–2.10(2H,m), 2.22–2.40(2H, m), 4.00–4.23(2H+keto 2H,m), 4.35–4.44(3H,m), 6.79(enol 1H,s), 7.20–7.58(7H+keto 1H,m), 7.77–7.83(2H,m), 8.10–8.20(1H,m), 8.32(enol 1H,d), 8.47(1H,d), 9.17–9.32 (4H,m), 9.70–9.82(enol 1H,brs)

EXAMPLE 10
(4R)-4-[(4-Guanidinomethylbenzoyl)amino]-5-[5-amidino-2-(2-carboxy-2-oxoethyl)phenoxy]pentanoic acid bistrifluoroacetate:

Step 1:
4-Guanidinomethylbenzoic acid:

A mixture of 1.51 g (10.0 mmol) of 4-aminomethylbenzoic acid, 20 ml of water, 2.0 ml of 28% aqueous ammonia and 1.00 g (23.8 mmol) of cyanamide was stirred at 60° C. overnight. The white precipitate thus formed was taken by the filtration, washed with water and dried to obtain the title compound.

Yield: 974 mg
MS (ESI,m/z) 194(M+H)+
H-NMR(DMSO-d6) δ4.37(2H,s), 7.23(2H,d), 7.81(2H, d), 7.90–8.45(4H,brs), 9.69(1H,s)

Step 2
(4R)-4-[(4-Guanidinomethylbenzoyl)amino]-5-[5-amidino-2-(2-carboxy-2-oxoethyl)phenoxy]pentanoic acid bistrifluoroacetate:

The title compound was obtained from 4-guanidinomethylbenzoic acid in the same manner as that in steps 5 and 6 in Example 1.

MS (ESI,m/z) 513(M+H)+
H-NMR(DMSO-d6) δ1.80–2.10(2H,m), 2.24–2.42(2H, m), 4.00–4.23 (2H+keto 2H,m), 4.35–4.44(3H,m), 6.79(enol 1H,s), 7.26–7.50(8H+keto 1H,m), 7.86(2H,d), 8.13(1H,t), 8.32(enol 1H,d), 8.42(1H,d), 9.15(2H,s), 9.26(2H,s)

EXAMPLE 11
(4R)-4-[(3-Guanidinocarbonylbenzoyl)amino]-5-[5-amidino-2-(2-carboxy-2-oxoethyl)phenoxy]pentanoic acid bistrifluoroacetate Step 1
3-Guanidinocarbonylbenzoic acid trifluoroacetate:

2.8 ml (5.6 mmol) of a solution of 2 M of oxalyl chloride in dichloromethane and 3 mg of dimethylformamide were added to 10 ml of a solution of 675 mg (3.8 mmol) of monomethyl isophthalate in dichloromethane under cooling with ice, and they were stirred at room temperature for 2 hours and then concentrated under reduced pressure to obtain the acid chloride.

2.8 ml (15.4 mmol) of a solution of 5.5 M of sodium methoxide in methanol was added to 10 ml of a solution of 1.83 g (18.7 mmol) of guanidine hydrochloride in methanol, and they were stirred at room temperature for 1 hour and then filtered through Celite. The filtrate was evaporated under reduced pressure. 10 ml of dimethylformamide was added to the residue, and they were stirred. The acid chloride synthesized as described above was added thereto together with 3 ml of dimethylformamide. They were stirred at room temperature for 30 minutes. 5% aqueous sodium hydrogencarbonate solution was added to the obtained mixture. After the extraction with ethyl acetate, the extract was dried over anhydrous sodium sulfate and concentrated under reduced pressure to obtain crude methyl 3-guanidinocarbonylbenzoate. 5.0 ml of ethanol and 2.0 ml (8.0 mmol) of aqueous solution of 4 M of sodium hydroxide were added to the product, and they were stirred at 60° C. for 2 hours. The solvent was evaporated, and the obtained residue was purified by the reversed phase HPLC in the same manner as that in step 5 in Example 1 to obtain the title compound.

Yield: 226 mg

MS (ESI,m/z) 206(M−H)−

H-NMR(DMSO-d6) δ7.34(4H,s), 7.47(1H,t), 8.02(1H,d), 8.18(1H,d), 8.83(1H,s)

Step 2

(4R)-4-[(3-Guanidinocarbonylbenzoyl)amino]-5-[5-amidino-2-(2-carboxy-2-oxoethyl)phenoxy]pentanoic acid bistrifluoroacetate:

The title compound was obtained from 3-guanidinocarbonylbenzoic acid trifluoroacetate in the same manner as that in steps 5 and 6 in Example 1.

MS (ESI,m/z) 527(M+H)+

H-NMR(DMSO-d6) δ1.80–2.00(2H,m), 2.23–2.43(2H, m), 3.95–4.55 (3H+keto 2H,m), 6.69(enol 1H,s), 7.35–7.43 (2H+keto 1H,m), 7.60–7.70(1H,m), 8.03(1H,d), 8.09(1H,d), 8.28(enol 1H,d), 8.30–8.56(3H,m), 8.63(1H,d), 8.90–9.30 (4H,m)

EXAMPLE 12

(4R)-4-[(1-Amidino-1,2,3,4-tetrahyddroquinoline-6-carbonyl)amino]-5-[5-amidino-2-(2-carboxy-2-oxoethyl) phenoxy]pentanoic acid bistrifluoroacetate:

Step 1

Ethyl 1,2,3,4-Tetrahydroquinoline-6-carboxylate:

257 mg (1.1 mmol) of nickel chloride hexahydrate and then 770 mg (20.3 mmol) of sodium borohydride were added to a mixture of 1.00 g (5.0 mmol) of ethyl quinoline-6-carboxylate and 15 ml of methanol under cooling with ice, and they were stirred at room temperature for 20 minutes. Methanol was evaporated, and the residue was purified by the silica gel column chromatography (hexane/ethyl acetate) to obtain the title compound.

Yield: 205 mg

H-NMR(CDCl3) δ1.35(3H,t), 1.93(2H,quint.), 2.78(2H, t), 3.36(2H,t), 4.30(2H,q), 6.40(1H,d), 7.63–7.68(2H,m)

Step 2

1-Amidino-1,2,3,4-tetrahydroquinoline-6-carboxylic acid trifluoroacetate:

A mixture of 200 mg (0.98 mmol) of ethyl 1,2,3,4-tetrahydroquinoline-6-carboxylate, 700 mg (6.1 mmol) of chloroformamidine hydrochloride and 2.0 g of dimethyl sulfone was stirred at 120° C. for 1 hour. After cooling to room temperature, 8.0 ml of methanol and 8.0 ml (32.0 mmol) of aqueous solution of 4 M of sodium hydroxide were added to the mixture, and they were stirred at room temperature for 2 days. After the concentration under reduced pressure, the residue was treated in the same manner as that in step 5 in Example 1 to obtain the title compound.

Yield: 97 mg

MS (ESI,m/z) 220(M+H)+

H-NMR(DMSO-d6) δ1.93(2H,quint.), 2.79(2H,t), 3.67 (2H,t), 7.40(1H,d), 7.78(1H,dd), 7.81(1H,d), 8.06(4H,s)

Step 3

(4R)-4-[(1-Amidino-1,2,3,4-tetrahydroquinoline-6-carbonyl)amino]-5-[5-amidino-2-(2-carboxy-2-oxoethyl) phenoxy]pentanoic acid bistrifluoroacetate:

The title compound was obtained from 1-amidino-1,2,3, 4-tetrahydroquinoline-6-carboxylic Acid Trifluoroacetate in the same manner as that in steps 5 and 6 in Example 1.

MS (ESI,m/z) 539(M+H)+

H-NMR(DMSO-d6) δ1.80–2.10(4H,m), 2.24–2.40(2H, m), 2.78(2H,t), 3.63(2H,t), 4.00–4.50(3H+keto 2H,m), 6.78 (enol 1H,s), 7.32–7.50(2H+keto 1H,m), 7.70–7.82(2H,m), 7.98(4H,s), 8.28–8.43(1H+enol 1H,m), 9.13(2H,s), 9.26 (2H,s), 9.76(enol 1H,s)

EXAMPLE 13

(4R)-4-[[3-(4-Amidinophenyl)benzoyl]amino]-5-[5-amidino-2-(2-carboxy-2-oxoethyl)phenoxy]pentanoic acid bistrifluoroacetate:

Step 1

Methyl 2-acetamido-3-[2-[(2R)-2-[(3-iodobenzoyl)amino]-4-benzyloxycarbonylbutoxy]-4-cyanophenyl]acrylate:

The title compound was obtained from 3-iodobenzoic acid in the same manner as that in step 5 in Example 1.

MS (ESI,m/z) 696(M+H)+

H-NMR(DMSO-d6) δ1.82–2.08(5H,m), 2.50–2.60(2H, m), 3.58(3H,s), 4.08–4.30(2H,m), 4.32–4.45(1H,m), 5.07 (2H,s), 7.16(1H,s), 7.22–7.45(7H,m), 7.63–7.72(2H,m), 7.82(1H,d), 7.89(1H,d), 8.15(1H,s), 8.45(1H,d), 9.63(1H,s)

Step 2

Methyl 2-acetamido-3-[2-[(2R)-2-[[3-(4-cyanophenyl) benzoyl]amino]-4-benzyloxycarbonylbutoxy]-4-cyanophenyl]acrylate:

72 mg (0.28 mmol) of bis(pinacolato)diboron, 6 mg (0.007 mmol) of [1,1'-bis(diphenylphosphino)ferrocene] dichloropalladium/dichloromethane complex, 4 mg (0.007 mmol) of 1,1'-bis(diphenylphosphino)ferrocene and 76 mg (0.78 mmol) of potassium acetate were successively added to a mixture of 180 mg of methyl 2-acetamido-3-[2-[(2R)-2-[(3-iodobenzoyl)amino]-4-benzyloxycarbonylbutoxy]-4-cyanophenyl]acrylate and 3.3 ml of dimethylformamide, and they were stirred in argon atmosphere at 80° C. for 6 hours.

After cooling to room temperature, 55 mg (0.30 mmol) of 4-bromobenzonitrile, 6 mg (0.007 mmol) of [1,1'-bis (diphenylphosphino)ferrocene]dichloropalladium/ dichloromethane complex and 0.8 ml (1.60 mmol) of an aqueous solution of 2 M of sodium carbonate were added to the obtained mixture, and they were stirred at 80° C. overnight. After the concentration under reduced pressure, the residue was purified by the reversed phase HPLC in the same manner as that in step 5 in Example 1 to obtain the title compound.

Yield: 66 mg

MS (ESI,m/z) 671(M+H)+

Step 3

(4R)-4-[[3-(4-Amidinophenyl)benzoyl]amino]-5-[5-amidino-2-(2-carboxy-2-oxoethyl)phenoxy]pentanoic acid bistrifluoroacetate:

The title compound was obtained from methyl 2-acetamido-3-[2-[(2R)-2-[(3-(4-cyanophenyl)benzoyl) amino]-4-benzyloxycarbonylbutoxy]-4-cyanophenyl] acrylate in the same manner as that in step 6 in Example 1.

MS (ESI,m/z) 560(M+H)+

H-NMR(DMSO-d6) δ1.82–2.20 (2H, m), 2.30–2.45 (2H, m), 4.08–4.52 (2H+keto 2H, m), 6.81 (enol 1H, s), 7.34–7.50 (2H+keto 1H, m), 7.58–7.64 (1H, m), 7.90–8.06 (6H, m), 8.17 (1H, s), 8.33 (enol 1H, d), 8.58 (1H, d), 9.07 (2H, s), 9.12 (2H, s), 9.26 (2H, s), 9.37 (2H, s)

EXAMPLE 14

(4R)-4-[[3-(4-Guanidinophenyl)benzoyl]amino]-5-[5-amidino-2-(2-carboxy-2-oxoethyl)phenoxy]pentanoic acid bistrifluoroacetate:

Step 1

Methyl 2-acetamido-3-[2-[(2R)-2-[[3-(4-aminophenyl) benzoyl]amino]-4-benzyloxycarbonylbutoxy]-4-cyanophenyl]acrylate trifluoroacetate:

The title compound was obtained by using 4-iodoaniline in place of 4-bromobenzonitrile in the same manner as that in step 2 in Example 13.

MS (ESI,m/z) 661(M+H)+

Step 2
Methyl 2-acetamido-3-[2-[(2R)-2-[[3-(4-guanidinophenyl) benzoyl]amino]-4-benzyloxycarbonylbutoxy]-4-cyanophenyl]acrylate trifluoroacetate:

A mixture of 340 mg (0.52 mmol) of methyl 2-acetamido-3-[2-[(2R)-2-[[3-(4-aminophenyl)benzoyl]amino]-4-benzyloxycarbonylbutoxy]-4-cyanophenyl]acrylate trifluoroacetate, 430 mg (3.74 mmol) of chloroformamidine hydrochloride and 2.0 g of dimethyl sulfone was stirred at 120° C. for 2 hours. Water was added to the reaction mixture. After washing with ethyl acetate, the aqueous layer was freeze-dried and purified by the reversed phase HPLC in the same manner as that in step 5 in Example 1 to obtain the title compound.

MS (ESI,m/z) 703(M+H)+

Step 3
(4R)-4-[[3-(4-Guanidinophenyl)benzoyl]amino]-5-[5-amidino-2-(2-carboxy-2-oxoethyl)phenoxy]pentanoic acid bistrifluoroacetate:

The title compound was obtained from methyl 2-acetamido-3-[2-[(2R)-2-[[3-(4-guanidinophenyl)benzoyl] amino]-4-benzyloxycarbonylbutoxy]-4-cyanophenyl] acrylate trifluoroacetate in the same manner as that in step 6 in Example 1.

MS (ESI,m/z) 575(M+H)+

H-NMR(DMSO-d6) δ1.82–2.15 (2H, m), 2.23–2.45 (2H, m), 4.05–4.48 (3H+keto 2H, m), 6.81 (enol 1H, s), 7.32–7.60 (9H+keto 1H, m), 7.76–7.92 (4H, m), 8.10 (1H, s), 8.33 (enol 1H, d), 8.53 (1H, d), 9.04 (2H, s), 9.26 (2H, s)

EXAMPLE 15

(4R)-4-[[3-(4-Aminophenyl)benzoyl]amino]-5-[5-amidino-2-(2-carboxy-2-oxoethyl)phenoxy]pentanoic acid bistrifluoroacetate:

The title compound was obtained from methyl 2-acetamido-3-[2-[(2R)-2-[[3-(4-aminophenyl)benzoyl] amino]-4-benzyloxycarbonylbutoxy]-4-cyanophenyl] acrylate trifluoroacetate in the same manner as that in step 6 in Example 1.

MS (ESI,m/z) 533(M+H)+

H-NMR(DMSO-d6) δ1.80–2.15(2H, m), 2.24–2.45 (2H, m), 4.05–4.48 (3H+keto 2H, m), 6.79 (2H, d), 6.82(enol 1H, s), 7.35–7.52 (5H+keto 1H, m), 7.71(2H, d), 7.99 (1H, s), 8.33 (enol 1H, d), 8.48 (1H, d), 8.98 (2H, s), 9.27 (2H, s)

EXAMPLE 16

(4R)-4-[[3-[5-(2-Amino)pyridyl]benzoyl]amino]-5-[5-amidino-2-(2-carboxy-2-oxoethyl)phenoxy]pentanoic acid bistrifluoroacetate:
Step 1
[3-[5-(2-Amino)pyridyl]benzoic acid hydrochloride:

1.02 g (4.0 mmol) of bis(pinacolato)diboron, 89 mg (0.1 mmol) of [1,1'-bis(diphenylphosphino)ferrocene] dichloropalladium/dichloromethane complex, 62 mg (0.1 mmol) of 1,1'-bis(diphenylphosphino)ferrocene and 1.06 g (10.9 mmol) of potassium acetate were successively added to a mixture of 1.00 g (3.6 mmol) of ethyl 3-iodobenzoate and 12 ml of dimethylformamide, and they were stirred in argon atmosphere at 80° C. overnight. After cooling to room temperature, 870 mg (4.1 mmol) of 2-acetylamino-5-bromopyridine, 90 mg (0.1 mmol) of [1,1'-bis (diphenylphosphino)ferrocene]dichloropalladium/ dichloromethane complex and 11.0 ml (22.0 mmol) of an aqueous solution of 2 M of sodium carbonate were added to the obtained mixture, and they were stirred at 80° C. overnight. The solvent was evaporated and the residue was purified by the silica gel column chromatography (hexane/ ethyl acetate) to obtain ethyl [3-[5-(2-amino)pyridyl] benzoate. 15.0 ml of 6 M hydrochloric acid and 5.0 ml of ethanol were added to the obtained product, and they were stirred at 80° C. overnight. The solvent was evaporated to obtain the title compound.

Yield: 198 mg
MS (ESI,m/z) 215(M+H)+
H-NMR(DMSO-d6) δ7.15(1H,d), 7.59(1H,t), 7.85–7.96 (2H,m), 8.14(1H,s), 8.16–8.26(2H,brs), 8.31(1H,dd), 8.36 (1H,d)

Step 2
(4R)-4-[[3-[5-(2-Amino)pyridyl]benzoyl]amino]-5-[5-amidino-2-(2-carboxy-2-oxoethyl)phenoxy]pentanoic acid bistrifluoroacetate:

The title compound was obtained from 3-[5-(2-amino) pyridyl]benzoic acid hydrochloride in the same manner as that in steps 5 and 6 in Example 1.

MS (ESI,m/z) 534(M+H)+

H-NMR(DMSO-d6) δ1.85–2.10(2H,m), 2.22–2.48(2H, m), 4.05–4.50 (3H+keto 2H,m), 6.80(enol 1H,s), 6.90–6.96 (1H,m), 7.35–7.60(4H+keto 1H,m), 7.76–7.85(2H,m), 8.04 (1H,s), 8.10–8.20(1H,m), 8.30–8.38(1H+enol 1H,m), 8.50 (1H,d), 9.06(2H,s), 9.26(2H,s)

EXAMPLE 17

(4R)-4-[3-[(4-Amidinophenoxy)methyl]benzoylamino]-5-[5-amidino-2-(2-carboxy-2-oxoethyl)phenoxy]pentanoic acid bistrifluoroacetate:
Step 1
Methyl 3-[(4-cyanophenoxy)methyl]benzoate:

500 mg (2.18 mmol) of methyl 3-bromomethylbenzoate, 437 mg (2.40 mmol) of 4-hydroxybenzonitrile and 600 mg of potassium carbonate were stirred in dimethylformamide at room temperature for 1.5 hours. The reaction mixture was filtered through Celite, then treated by an ordinary method and purified by the silica gel column chromatography to obtain the title compound.

Yield: 0.46 g (1.39 mmol)
H-NMR(CDCl3) δ3.90(3H, s), 5.15(2H, s), 7.05(2H, d), 7.50(1H, t), 7.60(2H, d), 7.60(1H, d), 8.05(1H, d), 8.10(1H, s)

Step 2
3-[(4-Cyanophenoxy)methyl]benzoic acid:

0.46 g of methyl 3-[(4-cyanophenoxy)methyl]benzoate and 175 mg of lithium hydroxide monohydrate were stirred in 7 ml of a solvent mixture of tetrahydrofuran, methanol and water (2:1:2) for 1 hour to hydrolyze the ester. The reaction mixture was added to 1 M of hydrochloric acid. The precipitate thus formed was taken by the filtration and then dried to obtain the title compound in the form of white crystals.

Yield: 0.38 g (1.16 mmol)
MS(ESI) m/z 252(M–H)–
H-NMR(CDCl3) δ5.20(2H, s), 7.05(2H, d), 7.52(1H, dd), 7.62(2H, d), 7.68(1H, d), 8.10(1H, d), 8.16(1H, s)

Step 3
(4R)-4-[3-[(4-Amidinophenoxy)methyl]benzoylamino]-5-[5-amidino-2-(2-carboxy-2-oxoethyl)phenoxy]pentanoic acid bistrifluoroacetate:

The title compound was obtained from 3-[(4-cyanophenoxy)methyl]benzoic acid in the same manner as that in steps 5 and 6 in Example 1.

MS(ESI,m/z) 590(M+H)+

H-NMR(DMSO-d6) δ1.80–2.20(2H, m), 2.25–2.50(2H, m), 4.00–4.60(3H+keto 2H, m), 5.25(2H, s), 6.80(enol 1H, s), 7.25(2H, d), 7.30–7.65(5H+keto 1H, m), 7.80(2H, d), 7.95(1H, s), 8.30(enol 1H, d), 8.50(1H, d), 8.80–9.34(8H, m)

EXAMPLE 18
(4R)-4-[3-[(3-Amidinophenoxy)methyl]benzoylamino]-5-[5-amidino-2-(2-carboxy-2-oxoethyl)phenoxy]pentanoic acid bistrifluoroacetate:

Step 1
3-[(3-Cyanophenoxy)methyl]benzoic acid:

The title compound was obtained in the same manner as that in steps 1 and 2 in Example 17 except that 4-hydroxybenzonitrile was replaced with 3-hydroxybenzonitrile.

MS(ESI) m/z 252(M−H)−

H-NMR(CDCl3) δ5.10(2H, s), 7.20(1H, d), 7.25(1H, s), 7.30(1H, d), 7.40(1H, t), 7.55(1H, t), 7.70(1H, d), 8.10(1H, d), 8.15(1H, d)

Step 2
(4R)-4-[3-[(3-Amidinophenoxy)methyl]benzoylamino]-5-[5-amidino-2-(2-carboxy-2-oxoethyl)phenoxy]pentanoic acid bistrifluoroacetate:

The title compound was obtained from 3-[(3-cyanophenoxy)methyl]benzoic acid in the same manner as that in steps 5 and 6 in Example 1.

MS(ESI,m/z) 590(M+H)+

H-NMR(DMSO-d6) δ1.80–2.20(2H, m), 2.30–2.50(2H, m), 4.00–4.60(3H+keto 2H, m), 5.20(2H, s), 6.80(enol 1H, s), 7.35–7.75(8H+keto 1H, m), 7.85(1H, d), 7.95(1H, s), 8.35(enol 1H, d), 8.50(1H, d), 9.10–9.65(8H, m), 9.80(enol 1H, s)

EXAMPLE 19
(4R)-4-(3-Phenylbenzoylamino)-5-[5-amidino-2-(2-carboxy-2-oxoethyl)phenoxy]pentanoic acid trifluoroacetate:

Step 1
Methyl 3-phenylbenzoate:

1.00 g (4.65 mmol) of methyl 3-bromobenzoate, 0.60 g (4.88 mmol) of phenylboronic acid, 161 mg (3 molar %) of tetrakistriphenylphosphine palladium and 2.0 g (18.6 mmol) of sodium carbonate were heated under reflux in 24 ml of a solvent mixture of toluene, ethanol and water (2/1/1) for 2 hours. The mixture was filtered through Celite, then after-treated by an ordinary method and purified by the silica gel column chromatography to obtain the title compound.

Yield: 0.90 g (4.25 mmol)

H-NMR(CDCl3) δ3.90(3H, s), 7.40(1H, t), 7.50(2H, t), 7.55(1H, t), 7.70(2H, t), 7.85(1H, d), 8.10(1H, d), 8.35(1H, s)

Step 2
3-Phenylbenzoic acid:

0.90 g of methyl 3-phenylbenzoate was fed into 20 ml of a solvent mixture of aqueous solution of 2 M of sodium hydroxide, tetrahydrofuran and methanol (4/2/1) to conduct the reaction at 70° C. for 2 hours. The solvent was evaporated, and the residue was fed into 3 M of hydrochloric acid. The precipitate thus formed was taken by the filtration and dried to obtain the title compound in the form of white crystals.

Yield: 0.43 g (2.17 mmol)

MS(ESI) m/z 197 (M−H)−

H-NMR(CDCl3) δ7.40(1H, t), 7.50(2H, t), 7.55(1H, t), 7.65(2H, d), 7.85(1H, d), 8.10(1H, d), 8.35(1H, s)

Step 3
(4R)-4-(3-Phenylbenzoylamino)-5-[5-amidino-2-(2-carboxy-2-oxoethyl)phenoxy]pentanoic acid trifluoroacetate:

The title compound was obtained from 3-phenylbenzoic acid in the same manner as that in steps 5 and 6 in Example 1.

MS(ESI) m/z 518(M+H)+

H-NMR(DMSO-d6) δ1.80–2.20(2H, m), 2.30–2.50(2H, m), 4.00–4.50(3H+keto 2H), 6.80(enol 1H, s), 7.20–7.85 (9H+keto 1H, m), 7.85–8.00 (2H, m), 8.30–8.50(1H+enol 1H, m), 8.85–9.35 (4H, m), 9.70(enol 1H, s)

EXAMPLE 20
(4R)-4-[[3-(3-Pyridyl)benzoyl]amino]-5-[5-amidino-2-(2-carboxy-2-oxoethyl)phenoxy]pentanoic acid bistrifluoroacetate:

Methyl 2-acetamido-3-[2-[(2R)-2-[[3-(3-pyridyl)benzoyl]amino]-4-benzyloxycarbonylbutoxy]-4-cyanophenyl]acrylate trifluoroacetate was obtained in the same manner as that in step 2 in Example 13 except that 4-bromobenzonitrile was replaced with 3-bromopyridine. Then this compound was treated in the manner as that in step 6 in Example 1 to obtain the title compound.

MS (ESI,m/z) 519(M+H)+

H-NMR(DMSO-d6) δ1.82–2.12(2H,m), 2.32–2.50(2H, m), 4.00–4.52 (3H+keto 2H,m), 6.80(enol 1H,s), 7.34–7.50 (2H+keto 1H,m), 7.56–7.65(2H,m), 7.87–7.94(2H,m), 8.16 (1H,s), 8.22(1H,d), 8.33(enol 1H,d), 8.54(1H,d), 8.65(1H,s), 8.99(3H,s), 9.25(2H,s)

EXAMPLE 21
(4R)-4-[[3-(4-Pyridyl)benzoyl]amino]-5-[5-amidino-2-(2-carboxy-2-oxoethyl)phenoxy]pentanoic acid bistrifluoroacetate:

Methyl 2-acetamido-3-[2-[(2R)-2-[[3-(4-pyridyl)benzoyl]amino]-4-benzyloxycarbonylbutoxy]-4-cyanophenyl]acrylate trifluoroacetate was obtained in the same manner as that in step 2 in Example 13 except that 4-bromobenzonitrile was replaced with 4-bromopyridine. Then this compound was treated in the manner as that in step 6 in Example 1 to obtain the title compound.

MS (ESI,m/z) 519(M+H)+

H-NMR(DMSO-d6) δ1.82–2.12(2H,m), 2.32–2.50(2H, m), 4.00–4.52(3H+keto 2H,m), 6.80(enol 1H,s), 7.34–7.52 (2H+keto 1H,m), 7.66(1H,t), 7.92–8.08(4H,m), 8.26(1H,s), 8.32(enol 1H,d), 8.60(1H,d), 8.75–8.84(2H,m), 9.00–9.17 (2H,m), 9.26(2H,s)

EXAMPLE 22
(4R)-4-[[1-(4-Pyridyl)-piperidine-3-carbonyl]amino]-5-[5-amidino-2-(2-carboxy-2-oxoethyl)phenoxy]pentanoic acid bistrifluoroacetate:

Step 1
Ethyl 1-(4-Pyridyl)-piperidine-3-carboxylate:

A mixture of 5 g of ethyl nipecotate, 4.8 g of 4-chloropyridine hydrochloride, 6.6 g of triethylamine and 100 ml of xylene was stirred at 100° C. overnight. The reaction mixture was treated with ethyl acetate as the extracting solvent in an ordinary manner, and the obtained residue was purified by the silica gel chromatography (ethyl acetate/ethanol) to obtain the title compound.

Yield: 1.8 g

H-NMR(CDCl3) δ1.25 (3H, t), 1.55–1.85 (3H, m), 2.05 (1H, m), 2.60 (1H, m), 3.00 (1H, m), 3.20 (1H, m), 3.65 (1H, m), 3.90 (1H, m), 4.15 (2H, m), 6.65 (2H, d), 8.25 (2H,d)

Step 2
1-(4-Pyridyl)-piperidine-3-carboxylic acid hydrochloride:

A mixture of 1.8 g of ethyl 1-(4-pyridyl)-piperidine-3-carboxylate, 50 ml of dioxane and 20 ml of 1 M hydrochloric acid was heated under reflux for 5 hours. The solvent was evaporated, and the residue was washed with ethyl acetate to obtain the title compound.

Yield: 1.84 g

H-NMR(DMSO-d6) δ1.45–2.05 (4H, m), 2.60 (1H, m), 3.30–4.05 (4H, m), 7.20 (2H, d), 8.20 (2H, d)

Step 3

(4R)-4-[[1-(4-Pyridyl)-piperidine-3-carbonyl]amino]-5-[5-amidino-2-(2-carboxy-2-oxoethyl)phenoxy]pentanoic acid bistrifluoroacetate:

A condensate was obtained from 1-(4-pyridyl)-piperidine-3-carboxylic acid hydrochloride in the same manner as that in step 5 in Example 1. Two kinds of diastereomers, a and b, were separated from each other by the reversed phase HPLC purification method. Each of them was treated in the same manner as that in step 6 in Example 1 to obtain the title compound.

Diastereomer a:

H-NMR(DMSO-d6) δ1.30–4.40 (16H+keto 2H, m), 6.76 (enol 1H), 7.20 (2H,d), 7.30–7.50 (2H+keto 1H), 8.04 (1H, d), 8.19 (2H, d), 8.32 (enol 1H, d), 9.18 (2H, br), 9.28 (2H, br), 9.75 (enol 1H, br), 13.40 (1H, br)

Diastereomer b:

MS (ESI,m/z) 526(MH+) 524(MH−)

H-NMR(DMSO-d6) δ1.30–4.40 (16H+keto 2H, m), 6.79 (enol 1H), 7.13 (2H, d), 7.30–7.50 (2H+keto 1H), 8.08 (1H, d), 8.17 (2H, d), 8.34 (enol 1H, d), 9.23 (2H, br), 9.31 (2H, br), 9.80 (enol 1H, br), 13.40 (1H, br)

EXAMPLE 23

(4R)-4-[(4-Guanidinobenzoyl)amino]-5-[5-amidino-2-(2-carboxy-2-oxoethyl)phenoxy]pentanoic acid bistrifluoroacetate:

The title compound was obtained from 4-guanidinobenzoic acid hydrochloride in the same manner as that in steps 5 and 6 in Example 1.

MS (ESI,m/z) 499(MH+) 497(MH−)

H-NMR(DMSO-d6) δ1.80–2.10 (2H, m), 2.25–2.40 (2H, m), 4.00–4.40 (3H+keto 2H, m), 6.80 (enol 1H, s), 7.25–7.50 (4H+keto 1H, m), 7.65 (4H, br), 7.95 (2H, d), 8.35 (enol 1H, d), 8.45 (1H, d), 9.10 (2H, br), 9.25 (2H, br), 9.75 (enol 1H, br), 10.10 (1H, s)

EXAMPLE 24

3-[4-Amidino-2-[2-(2-cyclopentyloxy-4-guanidinobenzoyl) aminoethoxy]-phenyl]-2-oxopropionic acid bistrifluoroacetate:

Step 1

4-(t-Butoxycarbonylamino)-2-hydroxybenzoic acid:

A mixture of 3.7 g of 4-amino-2-hydroxybenzoic acid, 11.9 g of di-t-butyl dicarbonate, 4.4 g of sodium hydroxide, 50 ml of water and 50 ml of dioxane was stirred at room temperature overnight. The reaction mixture was treated with ethyl acetate as the extracting solvent in an ordinary manner to obtain the title compound.

Yield: 2.21 g

H-NMR(DMSO-d6) δ1.50 (9H, s), 7.00 (1H, d), 7.10 (1H, s), 7.65 (1H, d), 9.70 (1H, s)

Step 2

Ethyl 4-(t-Butoxycarbonylamino)-2-hydroxybenzoate:

A mixture of 1.2 g of 4-(t-butoxycarbonylamino)-2-hydroxybenzoic acid, 900 mg of 1-[3-(dimethylamino)propyl]-3-ethylcarbodiimide hydrochloride (WSC·HCl), 550 mg of 4-dimethylaminopyridine, 1 ml of ethanol and 30 ml of dichloromethane was stirred at room temperature. The reaction mixture was treated with dichloromethane as the extracting solvent in an ordinary manner and then purified by the silica gel chromatography (ethyl acetate/hexane) to obtain the title compound.

Yield: 930 mg

H-NMR(CDCl3) δ1.40 (3H, t), 1.55 (9H, s), 4.40 (2H, q), 6.80 (1H, br), 6.90 (1H, br), 7.00 (1H, s), 7.75 (1H, d)

Step 3

4-(t-Butoxycarbonylamino)-2-cyclopentyloxybenzoic acid:

A mixture of 460 mg of ethyl 4-(t-butoxycarbonylamino)-2-hydroxybenzoate, 300 mg of cyclopentanol, 1.5 g of diethyl azodicarboxylate (40% solution in toluene), 900 mg of triphenylphosphine and 10 ml of tetrahydrofuran was stirred at room temperature for 3 days. The solvent was evaporated and the residue was purified by the silica gel chromatography (ethyl acetate/hexane) to obtain crude ethyl 4-(t-butoxycarbonylamino)-2-cyclopentyloxybenzoate. A mixture of this crude product, 20 ml of ethanol and 5 ml of 1 M aqueous sodium hydroxide solution was stirred at room temperature overnight. After the treatment with ethyl acetate as the extracting solvent in an ordinary manner, the title compound was obtained.

Yield: 380 mg

H-NMR(CDCl3) δ1.50 (9H, s), 1.70–2.20 (8H, m), 5.10 (1H, m), 6.70 (1H, d), 6.75 (1H, br), 7.60 (1H, s), 8.05 (1H, d)

Step 4

Methyl 2-acetamido-3-[2-[2-[4-(t-butoxycarbonylamino)-2-cyclopentyloxybenzoyl]aminoethoxy]-4-cyanophenyl]acrylate:

The title compound was obtained from 4-(t-butoxycarbonylamino)-2-cyclopentyloxybenzoic acid in the same manner as that in step 5 in Example 1.

H-NMR(CDCl3) δ1.50 (9H, s), 1.55–2.20 (8H, m), 2.05 (3H, s), 3.80 (3H, s), 3.85 (2H,dt), 4.20 (2H, t), 5.00 (1H, m), 6.67 (1H, s), 6.69 (1H, d), 7.16 (1H, s), 7.22 (1H, d), 7.40–7.56 (4H, m), 8.07 (1H, d), 8.29 (1H, s)

Step 5

Methyl 2-acetamido-3-[2-[2-[4-guanidino-2-cyclopentyloxy benzoyl]aminoethoxy]-4-cyanophenyl]acrylate trifluoro-acetate:

A mixture of 300 mg of methyl 2-acetamido-3-[2-[2-[4-(t-butoxycarbonylamino)-2-cyclopentyloxybenzoyl]aminoethoxy]-4-cyano-phenyl]acrylate and 10 ml of dioxane containing 4 M of hydrogen chloride was stirred at room temperature to remove t-butoxycarbonyl group. The solvent was evaporated. 7 ml of ethanol, 240 mg of cyanamide and 0.1 ml of concentrated hydrochloric acid were added to the residue, and they were stirred at 50° C. for 2 days. The solvent was evaporated, and the residue was purified by the reversed phase HPLC in the same manner as that in step 5 in Example 1 to obtain the title compound.

Yield: 60 mg

H-NMR(DMSO-d6) δ1.40–2.00 (11H, m), 3.65 (3H, s), 3.75 (2H, dt), 4.30 (2H, t), 4.95 (1H, m), 6.90 (1H, d), 6.96 (1H, s), 7.19 (1H, s), 7.46 (1H, d), 7.58–7.66 (5H, m), 7.72 (1H, d), 7.90 (1H, d), 8.19 (1H, t), 9.70 (1H, s), 9.95 (1H, s)

Step 6

3-[4-Amidino-2-[2-(2-cyclopentyloxy-4-guanidinobenzoyl) aminoethoxy]-phenyl]-2-oxopropionic acid bistrifluoroacetate:

The title compound was obtained from methyl 2-acetamido-3-[2-[2-[4-guanidino-2-cyclopentyloxybenzoyl]aminoethoxy]-4-cyanophenyl] acrylate trifluoroacetate in the same manner as that in step 6 in Example 1.

MS (ESI,m/z) 511(MH+) 509(MH−)

H-NMR(DMSO-d6) δ1.40–2.00 (8H, m), 3.60–3.90 (2H, m), 4.05 (keto 2H, s), 4.10–4.35 (2H, m), 4.95 (1H, m), 6.75 (enol 1H, s), 6.90 (1H, d), 6.95 (1H, s), 7.35–7.50 (2H+keto 1H, m), 7.75 (4H, br), 7.95 (1H, d), 8.30 (1H, t), 8.35 (enol 1H, d), 9.10 (2H, br), 9.25 (2H, br), 10.20 (1H, br)

EXAMPLE 25

3-[4-amidino-2-[2-(4-guanidino-2-Methoxybenzoyl) aminoethoxy]phenyl]-2-oxopropionic acid bistrifluoroacetate:

Step 1

Methyl 4-Guanidino-2-methoxybenzoate trifluoroacetate:

0.50 g (2.75 mmol) of methyl 4-amino-2-mMethoxybenzoate, 2.50 g of dimethyl sulfone and 1.74 g of chloroformamidine hydrochloride were mixed together, and the obtained mixture was stirred under heating at 120° C. for 1 hour. The reaction mixture was poured into water/ethyl acetate. The aqueous layer was concentrated, and the obtained residue was purified by the reversed-phase high-performance liquid chromatography in the same manner as that of step 5 in Example 1 to obtain the title compound.

MS(ESI)m/z 224(M+H)+

H-NMR(DMSO-d6) δ3.75(3H, s), 3.80(3H, s), 6.80(1, d), 7.65(4H, s), 7.70(2H, d)

Step 2

4-Guanidino-2-methoxybenzoic acid hydrochloride:

384 mg of methyl 4-guanidino-2-methoxybenzoate trifluoroacetate was dissolved in 8 ml of 3 M hydrochloric acid, and they were stirred at 80° C. for 2.5 hours. The solvent was evaporated to obtain the title compound.

Yield: 210 mg (1.00 mmol)

MS(ESI) m/z 210(M+H)+

H-NMR(DMSO-d6) δ3.82(3H, s), 6.82(1H, d), 6.95(1H, d), 7.70(1H, d), 7.70(4H, s), 10.2(1H, s)

Step 3

3-[4-Amidino-2-[2-(4-guanidino-2-methoxybenzoyl) aminoethoxy]phenyl]-2-oxopropionic acid bistrifluoroacetate:

A condensate of 4-guanidino-2-methoxybenzoic acid hydrochloride as the starting material and methyl 2-acetamido-3-[2-(2-aminoethoxy)-4-cyanophenyl]acrylate hydrochloride was obtained in the same manner as that in step 5 in Example 1. Then the procedure of step 6 in Example 1 was repeated to obtain the title compound.

MS (ESI,m/z) 457(MH+)

H-NMR(DMSO-d6) δ3.72–3.82(2H,m), 3.89(3H,s), 4.20–4.32(2H+keto 2H,m), 6.83(enol 1H,s), 6.90(1H,dd), 7.00(1H,d), 7.36–7.50(2H+keto 1H,m), 7.70(4H,s), 7.92 (1H,d), 8.34(enol 1H,d), 8.41(1H,t), 9.09(2H,s), 9.27(2H,s), 10.12(1H,s)

EXAMPLE 26

3-[4-Amidino-2-[2-(2-isopropoxybenzoyl)aminoethoxy] phenyl]-2-oxo-propionic acid trifluoroacetate:

Step 1

2-Isopropoxybenzoic acid:

5.00 g (36.2 mmol) of potassium carbonate and 3.27 g (26.6 mmol) of isopropyl bromide were added to a mixture of 2.00 g (13.2 mmol) of methyl salicylate and 10 ml of dimethylformamide, and they were stirred at room temperature overnight and then at 70° C. for 4 hours. 12.0 ml (36 mmol) of 3 M aqueous sodium hydroxide solution and 6.0 ml of ethanol were added to the reaction mixture, and they were stirred at 80° C. for 6 hours and then concentrated under reduced pressure. Water was added thereto. After washing with ethyl acetate, the aqueous layer was neutralized with hydrochloric acid. After the extraction with ethyl acetate, the extract was washed with water and saturated aqueous sodium chloride solution, dried over anhydrous sodium sulfate, and concentrated under reduced pressure to obtain the title compound.

Yield: 2.08 g

H-NMR(DMSO-d6) δ1.27(6H,d), 4.64(1H,m), 6.97(1H, t), 7.12(1H,d), 7.45(1H,t), 7.58(1H,d)

Step 2

3-[4-Amidino-2-[2-(2-isopropoxybenzoyl)aminoethoxy] phenyl]-2-oxopropionic acid trifluoroacetate:

A condensate of 2-isopropoxybenzoic acid as the starting material and methyl 2-acetamido-3-[2-(2-aminoethoxy)-4-cyanophenyl]acrylate hydrochloride was obtained in the same manner as that in step 5 in Example 1. Then the procedure of step 6 in Example 1 was repeated to obtain the title compound.

MS (ESI,m/z) 428(MH+)

H-NMR(DMSO-d6) δ1.25(6H,d), 3.78–3.85(2H,m), 4.20–4.33(2H+keto 2H,m), 4.78(1H,m), 6.83(enol 1H,s), 7.04(1H,t), 7.16(1H,d), 7.40–7.50(3H+keto 1H,m), 7.90 (1H,dd), 8.35(enol 1H,d), 8.50(1H,t), 9.01(2H,s), 9.27(2H, s), 9.70–9.85(enol 1H, brs)

EXAMPLE 27

(4R)-4-(2-Methoxy-5-phenylbenzoylamino)-5-[5-amidino-2-(2-carboxy-2-oxoethyl)phenoxy]pentanoic acid trifluoroacetate:

Step 1

Methyl 2-methoxy-5-iodobenzoate:

Methyl iodide (0.29 ml, 4.68 mmol) was added to a mixture of 1.0 g (3.60 mmol) of methyl 5-iodosalicylate, 0.50 g (3.60 mmol) of potassium carbonate and 4 ml of dimethylformamide, and they were stirred at room temperature for 3 hours. The reaction mixture was filtered through Celite and then after-treated in by an ordinary method to obtain the title compound.

Yield: 1.06 g (3.64 mmol)

Step 2

Methyl 2-Methoxy-5-phenylbenzoate:

1.06 g (3.64 mmol) of methyl 2-Methoxy-5-iodobenzoate, 460 mg (3.78 mmol) of phenylboronic acid, 83 mg (2 molar %) of tetrakistriphenylphosphine palladium and 1.52 g (14.4 mmol) of sodium carbonate were heated under reflux in 12 ml of toluene/ethanol/water (2/1/1) solvent mixture for 2 hours. After the filtration through Celite followed by the after treatment conducted by an ordinary method, the obtained residue was purified by the silica gel column chromatography to obtain the title compound.

Yield: 0.84 g (3.33 mmol)

Step 3

2-Methoxy-5-phenylbenzoic acid:

0.84 g (3.33 mmol) of methyl 2-Methoxy-5-phenylbenzoate was stirred under heating at 80° C. in a solvent mixture of dioxane/water containing 4 M of hydrogen chloride for 7 hours. The solvent was evaporated to obtain the title compound.

Yield: 0.65 g (2.86 mmol)

MS(ESI) m/z 229 (M+H)+

H-NMR(CDCl3) δ4.10(3H, s), 7.10(1H, d), 7.35(1H, t), 7.45(2H, t), 7.60(2H, d), 7.80(1H, d), 8.45(1H, s)

Step 4

(4R)-4-(2-Methoxy-5-phenylbenzoylamino)-5-[5-amidino-2-(2-carboxy-2-oxoethyl)phenoxy]pentanoic acid trifluoroacetate:

The title compound was obtained from 2-Methoxy-5-phenylbenzoic acid in the same manner as that in steps 5 and 6 in Example 1.

MS(ESI,m/z) 548(M+H)+

H-NMR(DMSO-d6) δ1.80–2.10(2H, m), 2.30–2.50(2H, m), 3.90(3H, s), 4.10–4.60(3H+keto 2H, m), 6.90(enol 1H, s), 7.20(1H, d), 7.30–7.50(5H+keto 1H, m), 7.60(2H,d), 7.80(1H, d), 7.95(1H, s), 8.30(enol 1H, d),8.35(1H, d), 9.10(2H, s), 9.25(2H, s)

EXAMPLE 28

(4R)-4-[(2-Aminobenzothiazole-6-carbonyl)amino]-5-[5-amidino-2-(2-carboxy-2-oxoethyl)phenoxy]pentanoic acid trifluoroacetate:

Step 1

2-Aminobenzothiazole-6-carboxylic acid hydrochloride:

500 mg of ethyl 2-aminobenzothiazole-6-carboxylate (Maybridge Co., UK) was stirred in 20 ml of 4 M hydrochloric acid at 80° C. for 5 hours. The solvent was evaporated, and the residue was washed with a solvent mixture of ethyl acetate/hexane to obtain the title compound.

Yield: 545 mg

H-NMR(DMSO-d6) δ7.60 (1H, d), 8.00 (1H, d), 8.50 (1H, s), 9.70 (2H, br)

Step 2

(4R)-4-[(2-Aminobenzothiazole-6-carbonyl)amino]-5-[5-amidino-2-(2-carboxy-2-oxoethyl)phenoxy]pentanoic acid trifluoroacetate:

The title compound was obtained from 2-aminobenzothiazole-6-carboxylic acid hydrochloride in the same manner as that in steps 5 and 6 in Example 1.

MS(ESI,m/z) 514(M+H)+

H-NMR(DMSO-d6) 1.80–2.15(2H, m), 2.25–2.50(2H, m), 4.00–4.50(3H+keto 2H, m), 6.80(enol 1H, s), 7.30–7.55 (3H+keto 1H,m), 7.75(1H, d), 7.95(2H, s), 8.15(1H, s), 8.25–8.40(1H+enol 1H, m), 9.00(2H, s), 9.25(2H, s), 9.75 (enol 1H, s)

The following compounds were obtained by the process described in the above Examples:

EXAMPLE 29

(3R)-3-[(2-Cyclopentyloxy-4-guanidinobenzoyl)amino]-4-[5-amidino-2-(2-carboxy-2-oxoethyl)phenoxy]butyric acid bistrifluoroacetate:

MS (ESI,m/z) 569(M+H)+

H-NMR(DMSO-d6) δ1.40–2.00 (8H, m), 2.80 (2H, m), 4.15–4.40 (2H+keto 1H, m), 4.75 (1H, m), 5.00 (1H, m), 6.80 (enol 1H, s), 6.90 (1H, d), 6.95 (1H, s), 7.35–7.55 (2H+keto 1H, m), 7.70 (4H, br), 7.95 (1H, d), 8.35 (enol 1H, d), 9.05–9.35 (4H, m), 9.80 (enol 1H, br), 10.10 (1H, s)

EXAMPLE 30

(4R)-4-[(4-Guanidinocarbonylbenzoyl)amino]-5-[5-amidino-2-(2-carboxy-2-oxoethyl)phenoxy]pentanoic acid bistrifluoroacetate:

MS (ESI,m/z) 527(M+H)+

H-NMR(DMSO-d6) δ1.82–2.10(2H,m), 2.25–2.48(2H, m), 4.00–4.25 (2H+keto 2H,m), 4.30–4.45(1H,m), 6.77(enol 1H,s), 7.30–7.48 (2H+keto1H,m), 7.92–8.12(4H, m), 8.15–8.40(2H+enol 1H,m), 8.60 (1H, d), 8.82–9.33(4H,m)

EXAMPLE 31

3-[4-Amidino-2-(2-(2-cyclobutoxybenzoylamino)ethoxy)phenyl]-2-oxopropionic acid trifluoroacetate:

MS(ESI) m/z 440(M+H)+

H-NMR(DMSO-d6) δ1.50–1.80 (2H, m), 1.90–2.20 (2H, m), 2.40 (2H, m), 3.60–3.85(2H, m), 4.00–4.40(2H+keto 2H, m), 4.80(1H, m), 6.80(enol 1H, s), 6.90–7.10 (2H+keto 1H, m), 7.30–7.50(3H, m), 7.70–7.90(1H, m), 8.35 (enol 1H, d), 8.40–8.60(1H, m), 9.20(4H, s)

EXAMPLE 32

(4R)-4-[3-Benzoylamino-benzoylamino]-5-[5-amidino-2-(2-carboxy-2-oxoethyl)phenoxy]pentanoic acid trifluoroacetate:

MS(ESI) m/z 561(M+H)+

H-NMR(DMSO-d6) δ1.80–2.20(2H.m), 2.25–2.60(2H, m), 4.00–4.50 (3H+keto 2H,m), 6.80(enol 1H, s), 7.30–7.70 (8H+keto 1H, m), 8.00(2H, d), 8.20(1H, s), 8.35(enol 1H, d), 8.45(1H, d), 9.00–9.40(4H, m), 10.4(1H, s)

EXAMPLE 33

(4R)-4-[3-(4-Methoxybenzoylamino)benzoylamino]-5-[5-amidino-2-(2-carboxy-2-oxoethyl)phenoxy]pentanoic acid trifluoroacetate:

MS(ESI) m/z 591(M+H)+

H-NMR(DMSO-d6) δ1.80–2.10(2H, m), 2.25–2.50(2H, m), 3.85(3H, s), 4.15–4.50(3H+keto 2H, m), 6.80(enol 1H, s), 7.05(2H, d), 7.30–7.60(5H+keto 1H, m), 7.95–8.10(2H, m), 8.15(1H, m), 8.35(enol 1H, d), 8.45(1H, d), 8.90(2H, s), 9.30(2H, s), 10.30(1H, s)

EXAMPLE 34

(4R)-4-[3-[(1-Imidazolyl)methyl]benzoylamino]-5-[5-amidino-2-(2-carboxy-2-oxoethyl)phenoxy]pentanoic acid bistrifluoroacetate MS(ESI) m/z 522(M+H)+

H-NMR(DMSO-d6) δ1.80–2.20(2H, m), 2.30–2.50(2H, m), 4.00–4.60(3H+keto 2H, m), 5.50(2H, s), 6.80(enol 1H, s), 7.35–7.95 (8H+keto 1H, m), 8.30(enol 1H, d), 8.50(1H, d), 9.10–9.25(5H, m)

EXAMPLE 35

(4R)-4-[(3-Acetylphenyl)benzoyl]amino]-5-[5-amidino-2-(2-carboxy-2-oxoethyl)phenoxy]pentanoic acid trifluoroacetate:

MS (ESI,m/z) 560(M+H)+

H-NMR(DMSO-d6) δ1.86–2.15(2H,m), 2.30–2.45(2H, m), 2.62(3H,s), 4.05–4.50 (3H+keto 2H,m), 6.82(enol 1H,s), 7.30–7.62(4H+keto 1H,m), 7.87 (2H,d), 7.91(2H,d), 8.07 (2H,d), 8.14(1H,s), 8.33(enol 1H,d), 8.55(1H,d), 8.92(2H,s), 9.25(2H,s)

EXAMPLE 36

(4R)-4-[(4-(1-Methylguanidino)benzoyl)amino]-5-[5-amidino-2-(2-carboxy-2-oxoethyl)phenoxy]pentanoic acid bistrifluoroacetate:

MS (ESI,m/z) 513(M+H)+

H-NMR(DMSO-d6) δ1.82–2.10(2H,m), 2.25–2.43(2H, m), 3.30(3H,s), 4.07–4.30(2H+keto 2H,m), 4.32–4.48(1H, m), 6.78(enol 1H,s), 7.30–7.60(8H+keto 1H,m), 8.00(2H,d), 8.31(enol 1H,d), 8.55(1H,d), 9.15–9.52(4H,m), 9.70–9.82 (enol 1H,brs)

EXAMPLE 37

(4R)-4-[(2-Amino-3,4-dihydroquinazoline-6-carbonyl)amino]-5-[5-amidino-2-(2-carboxy-2-oxoethyl)phenoxy]pentanoic acid bistrifluoroacetate:

MS (ESI,m/z) 511(M+H)+

H-NMR(DMSO-d6) δ1.80–2.10 (2H, m), 2.30–2.50 (2H, m), 4.00–4.40 (3H+keto 2H, m), 4.50 (2H, s), 6.75 (enol 1H, s), 7.00 (1H, d), 7.35–7.48 (2H+keto 1H, m), 7.66 (1H, s), 7.74 (1H, d), 7.85 (2H, s), 8.20–8.40 (1H+enol 1H, m), 8.53 (1H, s), 9.00 (2H, br), 9.25 (2H, br), 11.0 (1H, s)

EXAMPLE 38

N-[2-[2-(2-Benzylcarbamoyl-2-oxoethyl)-5-amidinophenoxy]ethyl]benzamide trifluoroacetate:

MS (ESI,m/z) 459(M+H)+

H-NMR(DMSO-d6) δ3.55 (2H, q), 4.15 (2H, t), 4.32 (2H, s), 4.35 (2H, d), 7.20–7.55 (11H, m), 7.85 (2H, d), 8.65 (1H, t), 9.10 (2H, br), 9.20 (1H, t), 9.30 (2H, br)

EXAMPLE 39

3-[4-Amidino-2-[2-(2-amino-benzothiazole-6-carbonyl)aminoethoxy]phenyl]-2-oxo-propionic acid trifluoroacetate:

A condensate of 2-aminobenzothiazole-6-carboxylic acid hydrochloride as the starting material and methyl 2-acetamido-3-[2-(2-aminoethoxy)-4-cyanophenyl]acrylate hydrochloride was obtained in the same manner as that in step 5 in Example 1. Then the procedure of step 6 in Example 1 was repeated to obtain the title compound.

MS(ESI,m/z) 442(M+H)+, 440(M−H)−

H-NMR(DMSO-d6) δ3.60–3.80(2H,m), 4.10–4.40(2H+keto 2H,m), 6.80(enol 1H,s), 7.25–8.00(5H+keto 1H,m), 8.15(1H,d), 8.30(enol 1H,d), 8.50–8.70(2H,br),9.00(2H,s), 9.30(2H,s), 9.65(enol1H,brs)

EXAMPLE 40
(4R)-4-[(2-Methoxy-5-iodobenzoyl)amino]-5-[5-amidino-2-(2-carboxy-2-oxoethyl)phenoxy]pentanoic acid trifluoroacetate:

Step 1
2-Methoxy-5-iodobenzoic acid:

Methyl 2-Methoxy-5-iodobenzoate obtained in step 1 in Example 27 was stirred in a solvent mixture (10 ml) of water and dioxane containing 4 N hydrogen chloride under heating at 80° C. for 3 hours. The solvent was evaporated to obtain the title compound.

Yield: 0.93 g

H-NMR(DMSO-d6) δ3.90(3H,s), 6.97(2H,d), 7.80(2H,d), 7.86(1H,s)

Step 2
(4R)-4-[(2-Methoxy-5-iodobenzoyl)amino]-5-[5-amidino-2-(2-carboxy-2-oxoethyl)phenoxy]pentanoic acid trifluoroacetate:

The title compound was obtained from 2-Methoxy-5-iodobenzoic acid in the same manner as that in steps 5 and 6 in Example 1.

MS(ESI,m/z) 598(M+H)+

H-NMR(DMSO-d6) δ1.70–2.10(2H,m), 2.20–2.45(2H,m), 3.80(3H,s), 4.00–4.50(3H+keto 2H,m) 6.83(enol 1H,s), 7.30–7.55(3H+keto 1H,m), 7.75(1H,d), 7.85(1H,d), 8.10(1H,m), 8.35(enol 1H,d), 9.00(2H,s), 9.25(2H,s), 9.80(enol 1H,brs)

EXAMPLE 41
(4R)-4-[(2-Methylbenzothiazole-6-carbonyl)amino]-5-[5-amidino-2-(2-carboxy-2-oxoethyl)phenoxy]pentanoic acid trifluoroacetate:

Step 1
2-Methylbenzothiazole-6-carboxylic acid:

Sodium sulfide nonahydrate (0.54 g) was dissolved in water (6 ml). Ethyl 4-amino-3-thiocyanatobenzoate (0.5 g) was added to the obtained solution, and they were heated under reflux for 30 minutes and then cooled to room temperature. A solid thus formed was filtered out, and the filtrate was neutralized with acetic acid. After the extraction with ethyl acetate, the obtained product was washed with saturated aqueous sodium chloride solution and then dried over anhydrous magnesium sulfate. The solvent was evaporated under reduced pressure. Triethyl orthoacetate (4 ml) was added to the residue, and they were stirred under heating at 100° C. for 5 hours. The solvent was evaporated, an the product was purified by the silica gel column chromatography. The obtained compound was stirred in a solvent mixture of water and dioxane containing 4 N hydrogen chloride under heating at 80° C. for 5 hours. The solvent was evaporated to obtain the title compound.

MS(ESI, m/z) 194(M+H)+, 192(M−H)−

H-NMR(CDCl3) δ2.90(3H,s), 8.00(1H,d), 8.15(1H,d), 8.60(1H,s)

Step 2
(4R)-4-[(2-Methylbenzothiazole-6-carbonyl)amino]-5-[5-amidino-2-(2-carboxy-2-oxoethyl)phenoxy]pentanoic acid trifluoroacetate:

The title compound was obtained from 2-methylbenzothiazole-6-carboxylic acid in the same manner as that in steps 5 and 6 in Example 1.

MS(ESI,m/z) 513(M+H)+

H-NMR(DMSO-d6) δ1.80–2.10(2H,m), 2.20–2.50(2H,m), 2.80(3H,s), 4.00–4.60(3H+keto 2H, m), 6.80(enol 1H,s), 7.30–7.50(2H+keto 1H,m), 7.95(1H,m), 8.30(enol 1H,d), 8.50(1H,s), 8.55(1H,d), 9.00(2H,s),9.25(2H,s), 9.75(enol 1H,brs)

EXAMPLE 42
(4R)-4-[(2-Methoxy-5-(thiophene-2-yl)benzoyl)amino]-5-[5-amidino-2-(2-carboxy-2-oxoethyl)phenoxy]pentanoic acid trifluoroacetate:

Step 1
Methyl 2-Methoxy-5-(thiophene-2-yl)benzoate:

The title compound was obtained in the same manner as that in step 2 in Example 27 except that phenylboronic acid used as the starting material was replaced with thiophene-2-boronic acid.

MS(ESI, m/z) 249(M+H)+

H-NMR(CDCl3) δ3.96(6H,s*2), 7.00(1H,d), 7.05(1H, dd), 7.24(1H,s), 7.25(1H,d), 7.70(1H,d), 8.00(1H,s)

Step 2
2-Methoxy-5-(thiophene-2-yl)benzoic acid:

Lithium hydroxide (43 mg) was added to methyl 2-Methoxy-5-(thiophene-2-yl)benzoate (102 mg) in a solvent mixture of tetrahydrofuran/methanol/water (2/1/1, 3 ml), and they were stirred overnight. The solvent was evaporated, and the residue was added to 3 N hydrochloric acid. The white solid thus precipitated was taken by the filtration as the title compound.

MS(ESI,m/z) 233(M−H)−

H-NMR(CDCl3) δ4.10(3H,s), 7.10(2H,d), 7.30(2H,dd), 7.80(1H,d), 8.44(1H,s)

Step 3
(4R)-4-[(2-Methoxy-5-(thiophene-2-yl)benzoyl)amino]-5-[5-amidino-2-(2-carboxy-2-oxoethyl)phenoxy]pentanoic acid trifluoroacetate:

The title compound was obtained from 2-Methoxy-5-(thiophene-2-yl)benzoic acid in the same manner as that in steps 5 and 6 in Example 1.

MS(ESI, m/z) 554(M+H)+

H-NMR(DMSO-d6) δ1.70–2.10(2H,m), 2.30–2.50(2H,m), 3.90(3H,s), 4.10–4.60(3H+keto 2H,m), 6.90(enol 1H,s), 7.10–7.25(2H,m), 7.35–7.65(3H+keto 1H,m), 7.75(1H,d), 7.90(1H,d), 8.20(1H,d), 8.30(enol 1H,d), 8.35(1H,d), 9.05(2H,s), 9.35(2H,s), 9.85(enol1H,brs)

EXAMPLE 43
(4R)-4-[(2-Methoxy-5-(thiophene-3-yl)benzoyl)amino]-5-[5-amidino-2-(2-carboxy-2-oxoethyl)phenoxy]pentanoic acid trifluoroacetate:

Step 1
Methyl 2-Methoxy-5-(thiophene-3-yl)benzoate:

The title compound was obtained in the same manner as that in step 2 in Example 27 except that phenylboronic acid used as the starting material was replaced with thiophene-3-boronic acid.

MS(ESI,m/z) 249(M+H)+

H-NMR(CDCl3) δ3.95(3H,s), 3.97(3H,s), 7.00(1H,d), 7.30–7.45(2H,d*2), 7.70(1H,d), 8.05(1H,s)

Step 2
2-Methoxy-5-(thiophene-3-yl)benzoic acid:

Methyl 2-Methoxy-5-(thiophene-3-yl)benzoate (124 mg) was dissolved in a solvent mixture of tetrahydrofuran/methanol/water (2/1/1, 3 ml). Lithium hydroxide (53 mg) was added to the obtained solution, and they were stirred overnight. The solvent was evaporated, and the residue was added to 3 N hydrochloric acid. The white solid thus precipitated was taken by the filtration as the title compound.

MS(ESI, m/z) 233(M−H)−

H-NMR(CDCl3) δ4.10(3H,s), 7.10(1H,d), 7.35–7.50(2H, m), 7.80(1H,d), 8.45(1H,s), 10.75(1H,brs)

Step 3

(4R)-4-[(2-Methoxy-5-(thiophene-3-yl)benzoyl)amino]-5-[5-amidino-2-(2-carboxy-2-oxoethyl)phenoxy]pentanoic acid trifluoroacetate:

The title compound was obtained from 2-Methoxy-5-(thiophene-3-yl)benzoic acid in the same manner as that in steps 5 and 6 in Example 1.

MS(ESI, m/z) 554(M+H)+

H-NMR(ESI) δ1.80–2.10(2H,m), 2.30–2.50(2H,m), 3.80 (3H,s), 4.10–4.60(3H+keto 2H,m), 6.85(enol 1H,s), 7.20 (1H,d), 7.35–7.85(5H+keto 1H,m), 8.00(1H,d), 8.15(1H,d), 8.30(enol 1H,d), 8.35(1H,d), 9.00(2H,s), 9.25(2H,d), 9.85 (enol 1H,brs)

EXAMPLE 44

(4R)-4-[(2,3-Dihydrobenzo[b]furan-6-carbonyl)amino]-5-[5-amidino-2-(2-carboxy-2-oxoethyl)phenoxy]pentanoic acid trifluoroacetate:

The title compound was obtained from 2,3-dihydrobenzo[b]furan-6-carboxylic acid in the same manner as that in steps 5 and 6 in Example 1.

MS(ESI, m/z) 484(M+H)+

H-NMR(DMSO-d6) δ1.80–2.10(2H,m), 2.30–2.50(2H, m), 3.20(2H,m), 4.00–4.80(5H+keto 2H,m), 6.83(enol 1H,s), 6.95(1H,dd), 7.40(3H+keto 1H,m), 7.60(1H,dd), 7.80 (enol 1H,d), 7.95(keto 1H,d), 8.32(enol 1H,d), 9.00(2H,s), 9.25(2H,s), 9.80(enol 1H,brs)

EXAMPLE 45

(4R)-4-[(5-Bromo-2,3-dihydrobenzo[b]furan-6-carbonyl)amino]-5-[5-amidino-2-(2-carboxy-2-oxoethyl)phenoxy]pentanoic acid trifluoroacetate:

The title compound was obtained from 5-bromo-2,3-dihydrobenzo[b]furan-6-carboxylic acid in the same manner as that in steps 5 and 6 in Example 1.

MS(ESI, m/z) 563(M+H)+

H-NMR(DMSO-d6) δ1.70–2.10(2H,m),2.30–2.50(2H, m), 3.25(2H,m), 4.00–4.80(5H+keto 2H,m), 6.80(enol 1H,s), 7.40(2H,m), 7.55(1H,s), 7.65(1H,s), 7.90(keto 1H,d), 8.32(enol 1H,d), 9.00(2H,s), 9.25(2H,s)

EXAMPLE 46

(4R)-4-[(5-Phenyl-2,3-dihydrobenzo[b]furan-6-carbonyl)amino]-5-[5-amidino-2-(2-carboxy-2-oxoethyl)phenoxy]pentanoic acid trifluoroacetate:

Step 1

Methyl 5-phenyl-2,3-dihydrobenzo[b]furan-6-carboxylate:

The title compound was obtained from 5-bromo-2,3-dihydrobenzo[b]furan-6-carboxylic acid (0.50 g) in the same manner as that in steps 1 and 2 in Example 27.

Yield: 0.51 g

MS(ESI) m/z, 255(M+H)+

H-NMR(CDCl3) δ3.30(2H,t), 3.90(3H,s), 4.75(2H,t), 7.30(1H,dd), 7.40(2H,dd*2), 7.50–7.65(3H,m), 7.95(1H,s)

Step 2

5-Phenyl-2,3-dihydrobenzo[b]furan-6-carboxylic acid:

The title compound was obtained from methyl 5-phenyl-2,3-dihydrobenzo[b]furan-6-carboxylate (150 mg) in the same manner as that in step 2 in Example 42.

Yield: 101 mg

MS(ESI) m/z, 239(M−H)−

H-NMR(CDCl3) δ3.40(2H,t), 4.85(2H,t), 7.35(1H,dd), 7.45(2H,dd*2), 7.55(2H,d*2), 7.65(1H,s), 8.20(1H,s)

Step 3

(4R)-4-[(5-Phenyl-2,3-dihydrobenzo[b]furan-6-carbonyl)amino]-5-[5-amidino-2-(2-carboxy-2-oxoethyl)phenoxy]pentanoic acid trifluoroacetate:

The title compound was obtained from 5-phenyl-2,3-dihydrobenzo[b]furan-6-carboxylic acid in the same manner as that in steps 5 and 6 in Example 1.

MS(ESI, m/z) 559(M+H)+

H-NMR(DMSO-d6) δ1.80–2.10(2H,m), 2.20–2.50(2H, m), 3.20–3.40(2H,m), 4.10–4.80(5H+keto 2H,m), 6.85(enol 1H,s), 7.30–7.65(7H+keto 1H,m), 7.70(1H,s), 7.85(1H,s), 8.00(1H,d), 8.35(enol 1H,d), 9.10(2H,s), 9.30(2H,s)

The structural formulae of the compounds in Referential Examples and Examples are as follows:

Compound of Referential Example 1

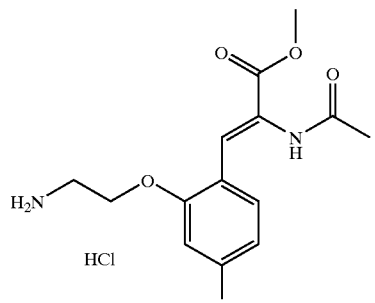

Compound of Referential Example 2

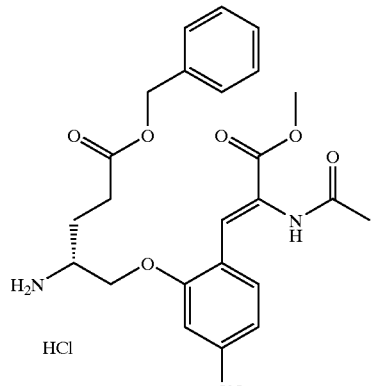

Compound of Example 1

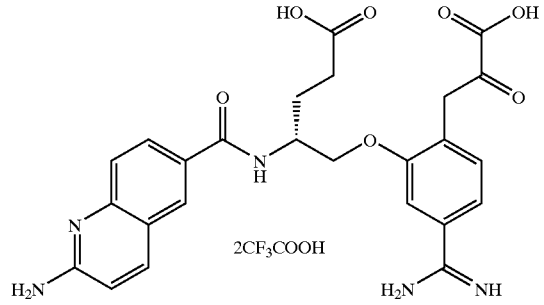

-continued
Compound of Example 2
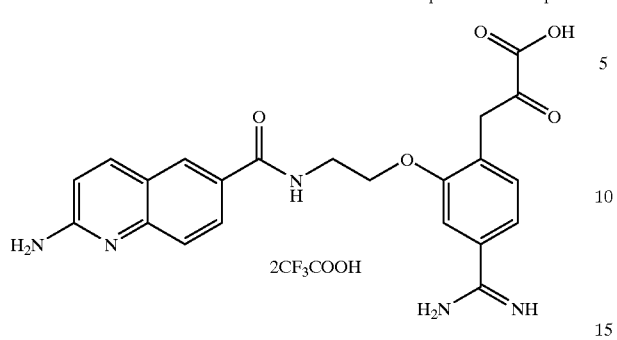
Compound of Example 3
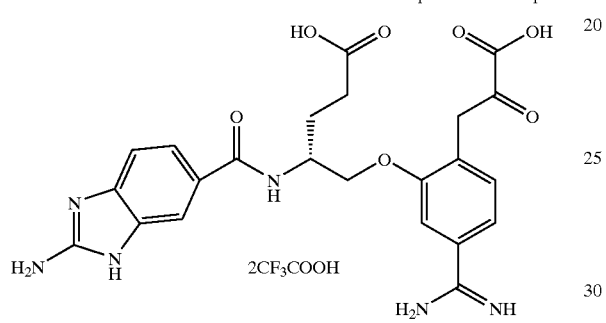
Compound of Example 4
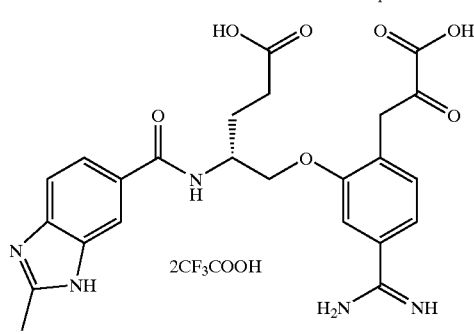
Compound of Example 5
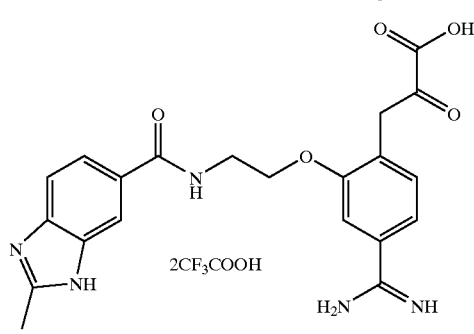
-continued
Compound of Example 6
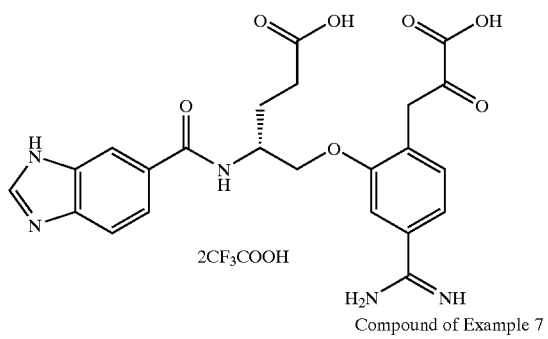
Compound of Example 7
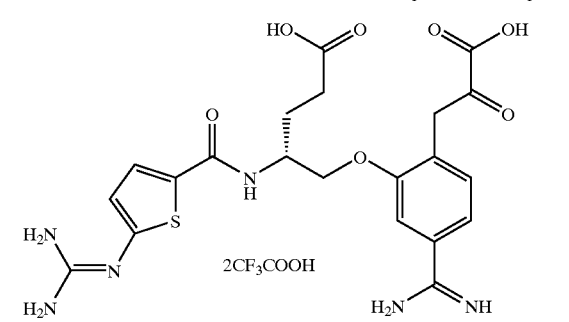
Compound of Example 8
Compound of Example 9
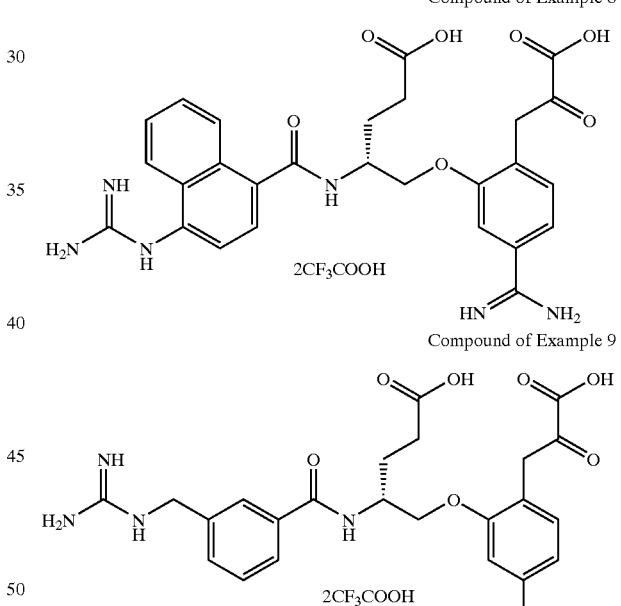
Compound of Example 10
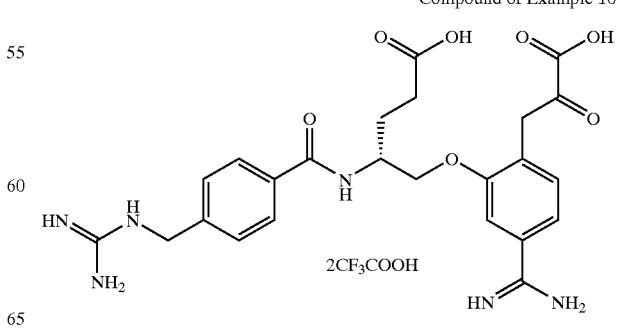

-continued
Compound of Example 11
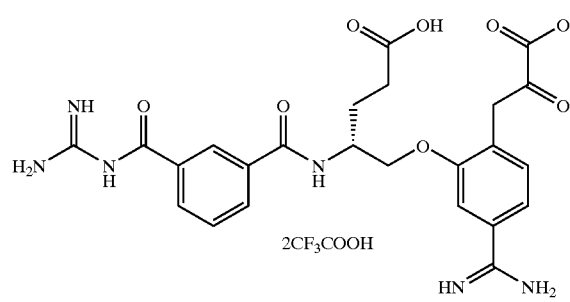
Compound of Example 12
Compound of Example 13
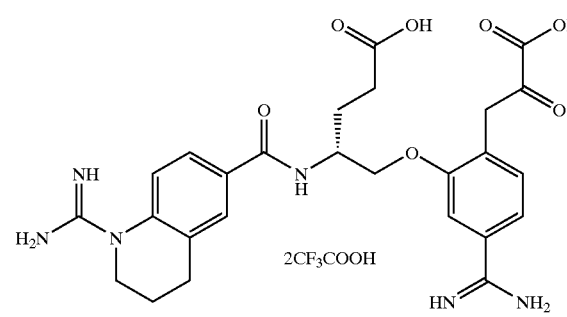
Compound of Example 14
Compound of Example 15
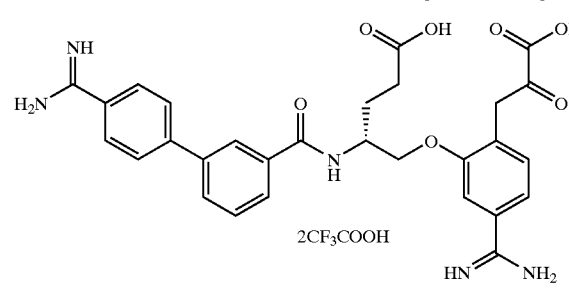
Compound of Example 16
Compound of Example 17
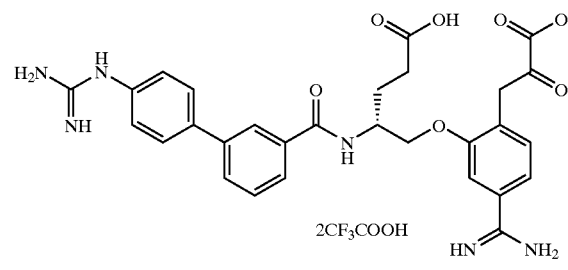
Compound of Example 18
Compound of Example 19
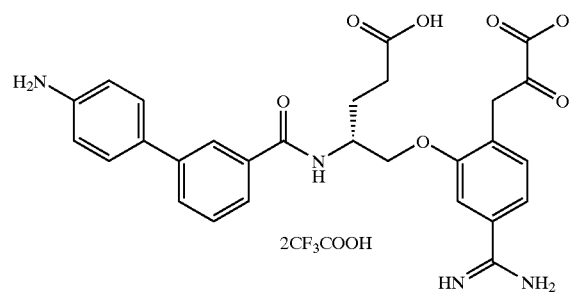

-continued

Compound of Example 20

Compound of Example 21

Compound of Example 22

Compound of Example 23

-continued

Compound of Example 24

Compound of Example 25

Compound of Example 26

Compound of Example 27

Compound of Example 28
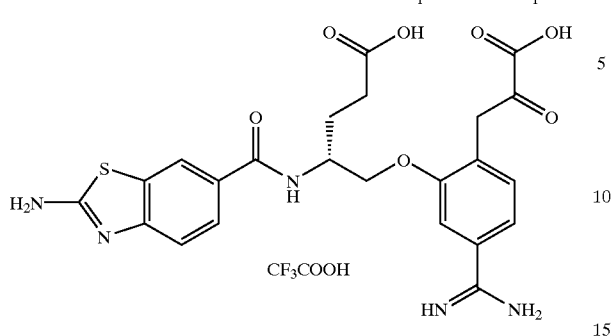
Compound of Example 29
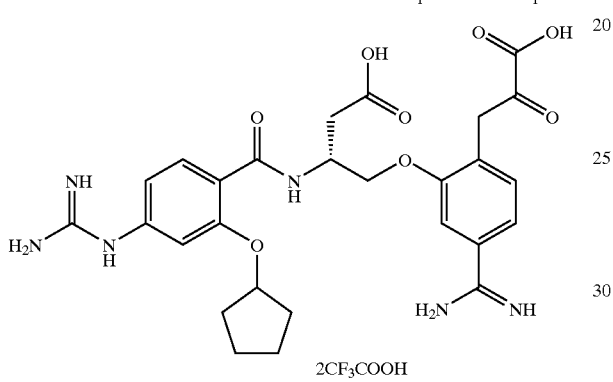
Compound of Example 30
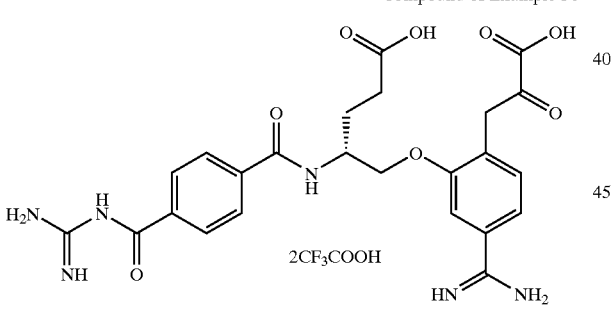
Compound of Example 31
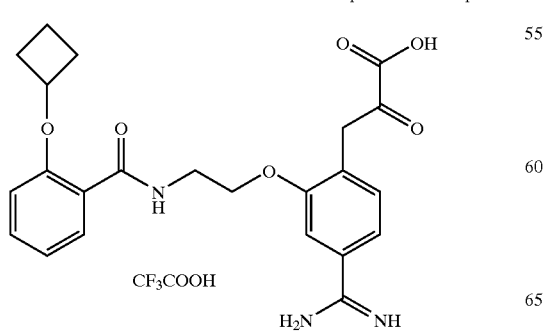
Compound of Example 32
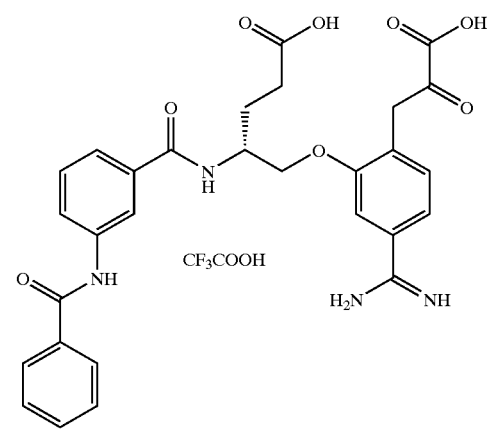
Compound of Example 33
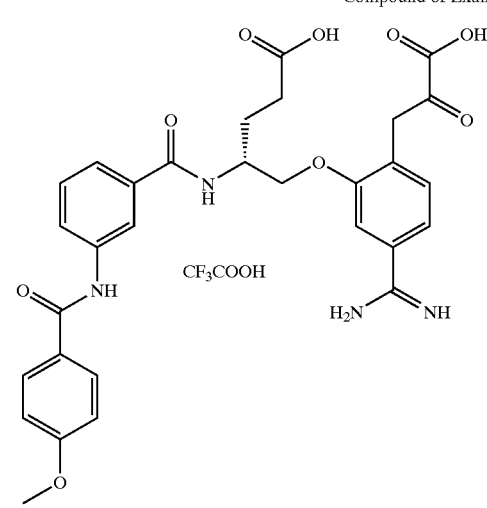
Compound of Example 34
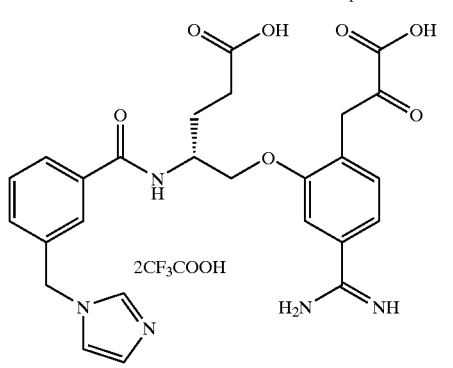
Compound of Example 35
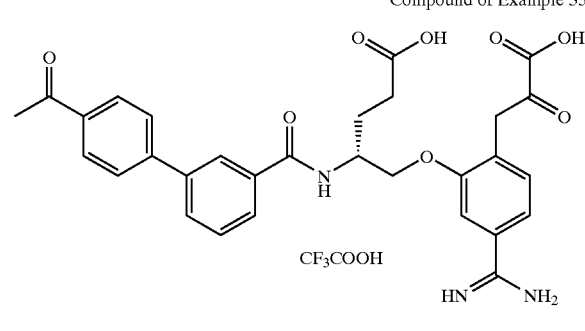

-continued
Compound of Example 36
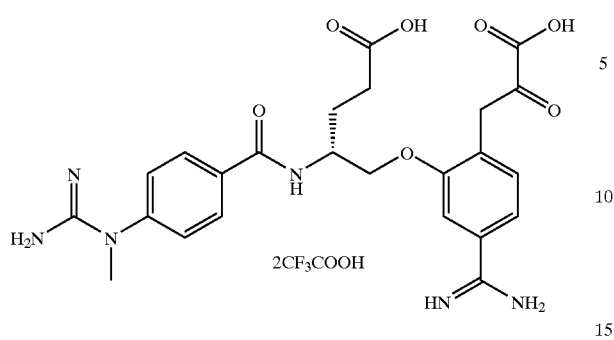
Compound of Example 37
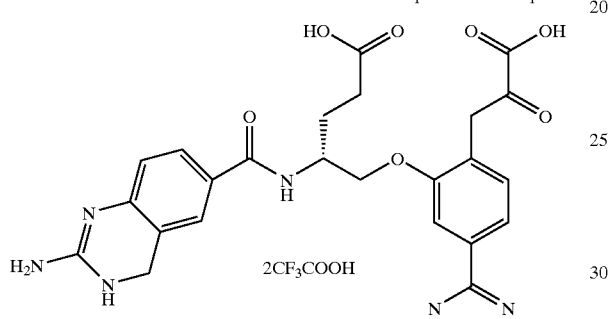
Compound of Example 38
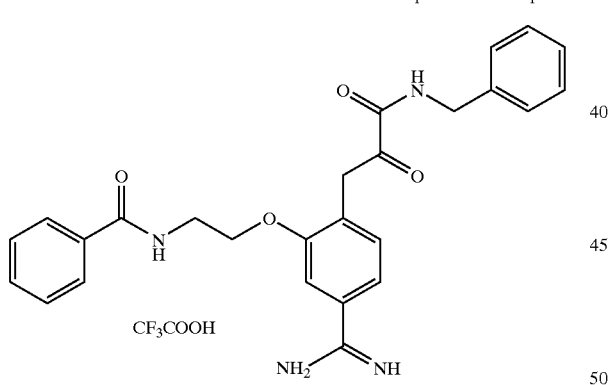
Compound of Example 39
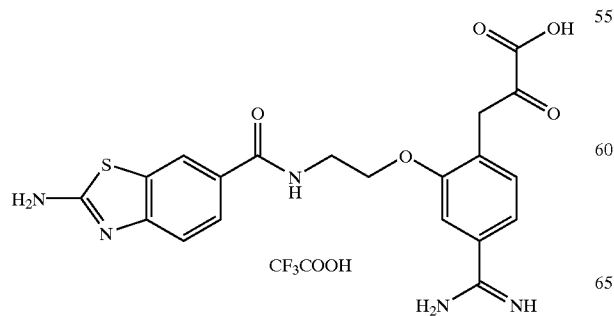
Compound of Example 40
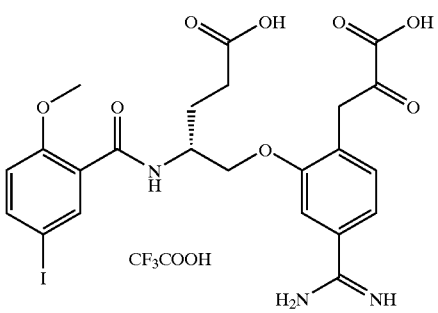
Compound of Example 41
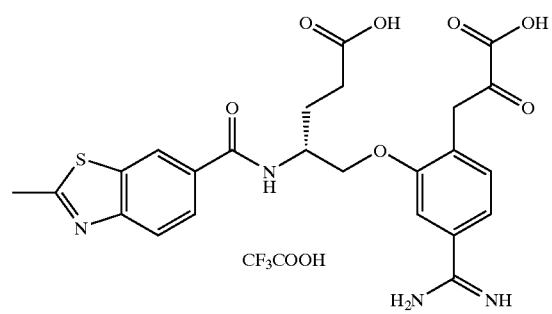
Compound of Example 42
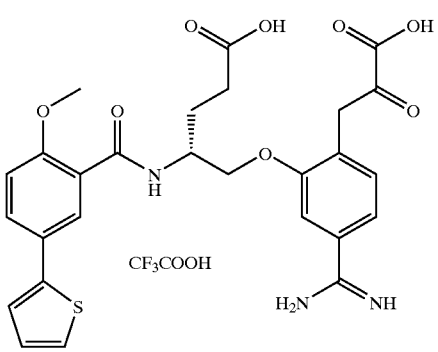
Compound of Example 43
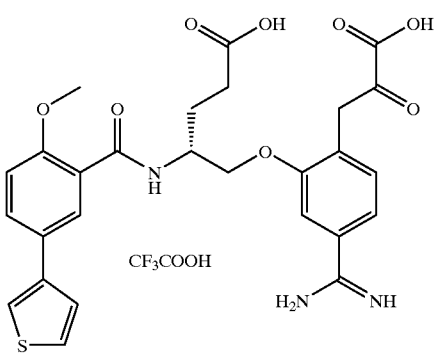

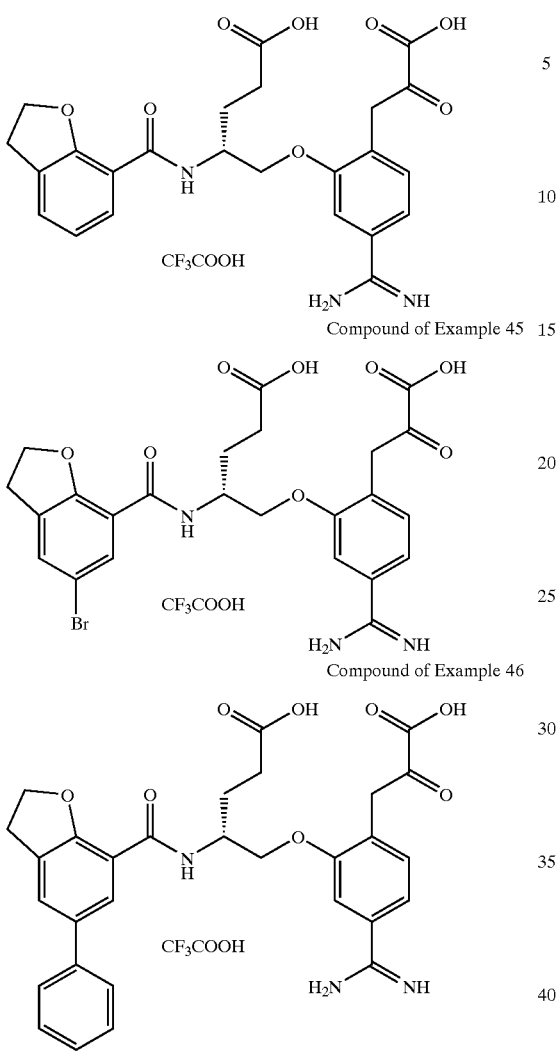

Compound of Example 44

Compound of Example 45

Compound of Example 46

What is claimed is:

1. Amidinophenylpyruvic acid compounds of the following formula (1) and pharmaceutically acceptable salts thereof:

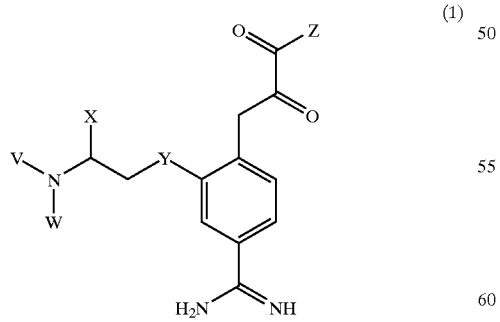

wherein

W represents a hydrogen atom or an alkyl group having 1 to 6 carbon atoms,

X represents a hydrogen atom, a carboxyalkyl group having 2 to 5 carbon atoms, or a methyl or ethyl group having a substituent(s) selected from the group consisting of alkoxycarbonyl groups having 2 to 8 carbon atoms, carbamoyl group, tetrazolyl group, sulfo group, sulfamoyl group, phosphono group and hydroxyl group, a benzyl group which may have a substituent(s) selected from the group consisting of hydroxyl group, carboxyl group, tetrazolyl group, sulfo group, sulfamoyl group, phosphono group, halogeno groups and alkyl groups having 1 to 3 carbon atoms, or an alkyl group having 1 to 4 carbon atoms, phenyl group, guanidinopropyl group, mercaptomethyl group, imidazolylmethl group, aminobutyl group, aminopropyl group, (methylthio)ethyl group or indolylmethyl group, X and W may be bonded together to form a ring, and in this cas, —W—X— represents an ethylene group, trimethylene group or tetramethylene group, V represents any of the following groups (1) to (8):
(1) a benzimidazolecarbonyl, quinolinecarbonyl, benzothiazolecarbonyl or benzoxazolecarbonyl group which may have a substituent(s) selected from the group consisting of an amino group(s), an alkyl group(s) having 1 to 6 carbon atoms, a halogeno group(s) and an alkoxyl group(s) having 1 to 6 carbon atoms,
(2) a benzoyl group substituted with phenyl, pyridyl or thiophenyl group having a substituent(s) selected from the group consisting of amidino group, guanidino group, amino group, dialkylamino groups having 2 to 5 carbon atoms, carboxyl group and acyl groups having 1 to 6 carbon atoms,
(3) a benzoyl group substituted with phenoxymethyl or benzoylamino group which may have a substituent(s) selected from the group consisting of amidino group, methoxyl group, guanidino group, amino group and dialkylamino groups having 2 to 5 carbon atoms,
(4) a guanidinocarbonylbenzoyl group or (guanidinomethyl)benzoyl group,
(5) a monoalkylguanidinobenzoyl group having 9 to 11 carbon atoms wherein the alkyl group bonded to the guanidino group may be also bonded to a benzoyl group to form a ring,
(6) a naphthalenecarboxylic, thiophenecarbonyl or 1-naphthalenesulfonyl group which may have a substituent(s) selected from the group consisting of guanidino group, guanidinocarbonyl group, guanidinomethyl group and amidino group,
(7) a benzoyl group which may have a substituent(s) selected from the group consisting of hydroxyl group, N-methylpyrrolidyloxy group, pyrrolidylmethyl group, imidazolylmethyl group and aminoimidazolylmethyl group, and
(8) a dihydrobenzofurancarbonyl or dihydrobenzopyrancarbonyl group which may have a substituent(s) selected from the group consisting of amidino group, guanidino group, amino group, alkyl groups having 1 to 6 carbon atoms, halogeno groups and aryl groups having 4 to 6 carbon atoms, groups (1) to (7) described above may further have an alkoxyl group having 1 to 6 carbon atoms on an aromatic carbon at the o-position to the carbonyl group or sulfonyl group bonded to N in formula (1), and when the alkyl group on the alkoxyl group has 2 or 3 carbon atoms, it may be bonded to a carbon atom on the aromatic ring to form a ring, Y represents an oxygen atom or sulfur atom, and Z represents a hydroxyl group or amino group which may have a substituent(s) selected from the group consisting of phenyl group, benzyl group and phenethyl group.

2. The amidinophenylpyruvic acid compounds and pharmaceutically acceptable salts thereof according to claim 1, wherein, in formula (1), W represents a hydrogen atom or an alkyl group having 1 to 3 carbon atoms, X represents a hydrogen atom or a carboxyalkyl group having 2 to 5 carbon atoms, V represents a benzimidazolecarbonyl, quinolinecarbonyl, dihydrobenzofurancarbonyl or benzothiazolecarbonyl group which may have a substituent(s) selected from the group consisting of an amino group(s), an alkyl group(s) having 1 to 6 carbon atoms, a halogeno group(s), phenyl group and an alkoxyl group(s) having 1 to 6 carbon atoms, a benzoyl group substituted with phenyl, pyridyl or thiophenyl group having a substituent(s), at the 3-position thereof, the substituent being selected from the group consisting of amidino group, guanidino group and amino group, a benzoyl group substituted with phenoxymethyl group having a substituent(s), at the 3-position thereof, the substituent being selected from the group consisting of amidino group, guanidino group and amino group, a guanidinocarbonylbenzoyl group or (guanidinomethyl)benzoyl group, naphthalenecarbonyl or thiophenecarbonyl group having a substituent(s) selected from the group consisting of guanidino group, guanidinocarbonyl group and guanidinomethyl group, or monoalkylguanidinobenzoyl group having 9 to 11 carbon atoms, wherein the alkyl group bonded to guanidino group may be also bonded to the benzoyl group to form a ring, and Z represents a hydroxyl group.

3. The amidinophenylpyruvic acid compounds and pharmaceutically acceptable salts thereof according to claim 1, wherein V represents any of groups (1) to (7) wherein an aromatic carbon at the o-position to carbonyl group or sulfonyl group bonded to N in formula (1) may further have an alkoxyl group having 1 to 6 carbon atoms.

4. The amidinophenylpyruvic acid compounds and pharmaceutically acceptable salts thereof according to claim 3, wherein, in formula (1), W represents a hydrogen atom or an alkyl group having 1 to 3 carbon atoms, X represents a hydrogen atom or a carboxyalkyl group having 2 to 5 carbon atoms, V represents a benzimidazolecarbonyl, quinolinecarbonyl or benzothiazolecarbonyl group which may have a substituent(s) selected from the group consisting of an amino group(s), an alkyl group(s) having 1 to 6 carbon atoms, a halogeno group s) and an alkoxyl group(s) having 1 to 6 carbon atoms, a benzoyl group substituted with phenyl, pyridyl or thiophenyl group having a substituent(s), at the 3-position thereof, the substituent being selected from the group consisting of amidino group, guanidino group and amino group, a benzoyl group substituted with phenoxymethyl group having a substitute(s), at the 3-position thereof, the substituent being selected from the group consisting of amidino group, guanidino group and amino group, a guanidinocarbonylbenzoyl group or (guanidinomethyl)benzoyl group, naphthalenecarbonyl or thiophenecarbonyl group having a substituent(s) selected from the group consisting of guanidino group, guanidinocarbonyl group and guanidinomethyl group, or a monoalkylguanidinobenzoyl group having 9 to 11 carbon atoms, wherein the alkyl group bonded to guanidino group may be also bonded to benzoyl group to form a ring, and Z represents hydroxyl group.

5. The amidinophenylpyruvic acid compounds and pharmaceutically acceptable salts thereof according to claim 2, wherein W in formula (1) represents a hydrogen atom and Y represents an oxygen atom.

6. The amidinophenylpyruvic acid compounds and pharmaceutically acceptable salts thereof according to claim 2, wherein X in formula (1) represents a carboxyethyl group.

7. The amidinophenylpyruvic acid compounds and pharmaceutically acceptable salts thereof according to claim 2, wherein, in formula (1), X represents a hydrogen atom, carboxymethyl group or carboxyethyl group, V represents a benzimidazole-5-carbonyl, quinoline-6-carbonyl, 2,3-dihydrobenzofuran-6-carbonyl or benzothiazole-6-carbonyl group which may have a substituent(s) selected from the group consisting of an amino group(s), an alkyl group(s) having 1 to 6 carbon atoms, phenyl group, a halogeno group(s) and an alkoxyl group(s) having 1 to 6 carbon atoms, a benzoyl group substituted with phenyl, pyridyl or thiophenyl group having a substituent(s), at the 3-position thereof, the substituent being selected from the group consisting of amidino group and guanidino group, benzoyl group substituted with phenoxymethyl group which may have a substituent(s), at the 3-position hereof, the substituent being selected from the group consisting of amidino group an guanidino group, 3-guanidinocarbonylbenzoyl or 3-guanidinomethylbenzoyl group, or 1-amidino-1,2,3,4-tetrahydroquinoline-6-carbonyl group.

8. The amidinophenylpyruvic acid compounds and pharmaceutically acceptable salts thereof according to claim 4, wherein, in formula (1), X represents a hydrogen atom, carboxymethyl group or carboxyethyl group, and V represents a benzimidazole-5-carbonyl, quinoline-6-carbonyl or benzothiazole-6-carbonyl group which may have a substituent(s) selected from the group consisting of an amino group(s), an alkyl group(s) having 1 to 6 carbon atoms, a halogeno group(s) and an alkoxyl group(s) having 1 to 6 carbon atoms, a benzoyl group substituted with phenyl, pyridyl or thiophenyl group having a substituent(s), at the 3-position thereof, the substituent being selected from amidino group and guanidino group, a benzoyl group substituted with phenoxymethyl group which may have a substituent(s), at the 3-position thereof, the substituent being selected from amidino group and guanidino group, 3-guanidinocarbonylbenzoyl or 3-guanidinomethylbenzoyl group, or 1-amidino-1,2,3,4-tetrahydroquinoline-6-carbonyl group.

9. The amidinophenylpyruvic acid compounds and pharmaceutically acceptable salts thereof according to claim 2, wherein X represents a hydrogen atom, carboxymethyl group or carboxyethyl group, V represents a benzimidazole-5-carbonyl, quinoline-6-carbonyl or benzothiazole-6-carbonyl group which may have a substituent(s) selected from the group consisting of an amino group(s) and an alkyl group(s) having 1 to 3 carbon atoms, a benzoyl group substituted with phenyl or pyridyl group having a substituent(s), at the 3-position thereof, the substituent being selected from amidino group and guanidino group, 3-guanidinocarbonylbenzoyl group, or 1-amidino-1,2,3,4-tetrahydroisoquinoline-6-carbonyl group.

10. The amidinophenylpyruvic acid compounds and pharmaceutically acceptable salts thereof according to claim 1, wherein, in formula (1), W represents a hydrogen atom, X represents a hydrogen atom or carboxyethyl group, V represents a benzimidazole-5-carbonyl, quinoline-6-carbonyl or benzothiazole-6-carbonyl group which may have a substituent(s) selected from the group consisting of an amino group(s) and an alkyl group(s) having 1 to 3 carbon atoms, Y represents an oxygen atom, and Z represents a hydroxyl group.

11. The amidinophenylpyruvic acid compounds and pharmaceutically acceptable salts thereof according to claim 1, wherein, in formula (1), W represents a hydrogen atom, X represents a hydrogen atom or carboxyethyl group, V represents a 3-guanidinocarbonylbenzoyl group, 3-guanidinomethylbenzoyl group, 3-(4-amidinophenoxymethyl)benzoyl group, benzimidazole-5-carbonyl group, 2-methylbenzimidazole-5-carbonyl group, 2-aminobenzimidazolecarbonyl group, 2-aminoquinoine-6-carbonyl group, 3-(4-amidinophenyl)benzoyl group, 3(4-guanidinophenyl)benzoyl group, 1-amidino-1,2,3,4-tetrahydroquinoline-6-carbonyl group or 2-aminobenzothiazole-6-carbonyl group, Y represents an oxygen atom, and Z represents a hydroxyl group.

12. The amidinophenylpyruvic acid compounds and pharmaceutically acceptable salts thereof according to claim 1, wherein W represents a hydrogen atom, X represents a carboxyethyl group, V represents a 2-methylbenzimidazole-5-carbonyl group, 2-aminobenzimidazole-5-carbonyl group, 2-aminoquinoline-6-carbonyl group or 2-aminobenzothiazole-6-carbonyl group, Y represents an oxygen atom and Z represents a hydroxyl group.

13. Amidinophenylpyruvic acid compounds of the following formula (1–2) and pharmaceutically acceptable salts thereof:

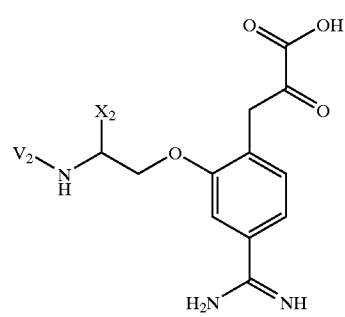

(1-2)

wherein $X_2$ represents a hydrogen atom, carboxymethyl group or arboxyethyl group, and $V_2$ represents a benzoyl group having a substituent(s) selected from the group consisting of alkoxyl groups having 1 to 5 carbon atoms at the o-position to the carbonyl group in benzoyl group, iodine atom or phenyl, thiophenyl, pyridyl or guanidino group at the p-position to the carbonyl group in benzoyl group, or guanidino or amino group at the p-position to the carbonyl group in benzoyl group, or $V_2$ represents 1(4-pyridyl)piperidine-3-carbonyl group or indole-5-carbonyl group, and wherein the substituent at the m-position to the carbonyl group in the substituent-containing benzoyl group $V_2$ is phenyl, thiophenyl pyridyl or guanidino group.

14. A pharmaceutical composition containing the amidinophenylpyruvic acid compound or the salt thereof according to claim 1 as the active ingredient.

15. A pharmaceutical composition containing the amidinophenylpyruvic acid compound or the salt thereof according to claim 2 as the active ingredient.

16. A pharmaceutical composition containing the amidinophenylpyruvic acid compound or the salt thereof according to claim 3 as the active ingredient.

17. A pharmaceutical composition containing the amidinophenylpyruvic acid compound or the salt thereof according to claim 4 as the active ingredient.

18. A pharmaceutical composition containing the amidinophenylpyruvic acid compound or the salt thereof according to claim 5 as the active ingredient.

19. A pharmaceutical composition containing the amidinophenylpyruvic acid compound or the salt thereof according to claim 6 as the active ingredient.

20. A pharmaceutical composition containing the amidinophenylpyruvic acid compound or the salt thereof according to claim 7 as the active ingredient.

21. A pharmaceutical composition containing the amidinophenylpyruvic acid compound or the salt thereof according to claim 8 as the active ingredient.

22. A pharmaceutical composition containing the amidinophenylpyruvic acid compound or the salt thereof according to claim 9 as the active ingredient.

23. A pharmaceutical composition containing the amidinophenylpyruvic acid compound or the salt thereof according to claim 10 as the active ingredient.

24. A pharmaceutical composition containing the amidinophenylpyruvic acid compound or the salt thereof according to claim 11 as the active ingredient.

25. A pharmaceutical composition containing the amidinophenylpyruvic acid compound or the salt thereof according to claim 12 as the active ingredient.

26. A pharmaceutical composition containing the amidinophenylpyruvic acid compound or the salt thereof according to claim 13 as the active ingredient.

27. A method of treating diseases caused by the blood coagulation, thrombus, embolus, intimal thickening or angiostenosis, which comprises the step of administering the pharmaceutical composition of claim 14 to a patient suffering from the disease.

28. A method of treating disease caused by the blood coagulation, thrombus, embolus, intimal thickening or angiostenosis, which comprises the step of administering the pharmaceutical composition of claim 26, to a patient suffering from the disease.

29. A method of treating disseminated intravascular coagulation, deep vein thrombosis, diseases caused by pulmonary vascular disorder, diseases caused by an ischemic heart disease, diseases caused by cerebrovascular disorder, occlusion of blood vessel and angiostenosis after an operation for forming a bypass in coronary artery, coronary artery intervention after percutaneous transluminal coronary angioplasty (PTCA), occlusion of blood vessel and angiostenosis after percutaneous transluminal coronary recanalization (PTCR), formation of thrombi after artificial blood vessel-forming operation or artificial valve replacement, peripheral embolism, formation of thrombi in the course of the extracorporeal circulation and antiphospholipid antibody syndrome, which comprises the step of administering the pharmaceutical opposition of claim 14 to a patient suffering from the disease.

30. A method of treating disseminated intravascular coagulation, deep vein thrombosis, diseases caused by pulmonary vascular disorder, diseases caused by an ischemic heart disease, diseases caused by a cerebrovascular disorder, occlusion of blood vessel and angiostenosis after an operation for forming a bypass in coronary artery, coronary artery intervention after percutaneous transluminal coronary angioplasty (PTCA), occlusion of blood vessel and angiostenosis after percutaneous transluminal coronary recanalization (PTCR), formation of thrombi after artificial blood vessel-forming operation or artificial valve replacement, peripheral embolism, formation of thrombi in the course of the extracorporeal circulation and antiphospholipid antibody syndrome, which comprises the step of administering the pharmaceutical composition of claim 26 to a patient suffering from the disease.

31. A method of treating cerebral infarction or cerebral stroke, which comprises the step of administering the pharmaceutical composition of claim 14 to a patient suffering the disease.

32. A method of treating cerebral infarction or cerebral stroke, which comprises the step of administering the pharmaceutical composition of claim 26 to a patient suffering the disease.

33. An antagonist against activated blood coagulation factor VII (FVIIa), which contains the amidinophenylpyruvic acid compound or the salt thereof according to claim 1 as the active ingredient.

34. An antagonist against activated blood coagulation factor VII (FVIIa), which contains the amidinophenylpyruvic acid compound or the salt thereof according to claim 13 as the active ingredient.

* * * * *